(12) United States Patent
Nomoto et al.

(10) Patent No.: US 6,853,477 B2
(45) Date of Patent: Feb. 8, 2005

(54) PARTICLES FOR ELECTROPHORESIS, A PRODUCTION METHOD THEREOF AND A DISPLAY USING THE PARTICLES

(75) Inventors: Tsuyoshi Nomoto, Tokyo (JP); Tetsuya Yano, Kanagawa (JP); Shinya Kozaki, Tokyo (JP); Tsutomu Honma, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 260 days.

(21) Appl. No.: 10/133,405

(22) Filed: Apr. 29, 2002

(65) Prior Publication Data

US 2003/0206330 A1 Nov. 6, 2003

(30) Foreign Application Priority Data

Apr. 27, 2001 (JP) .......................... 2001-131824
Jul. 10, 2001 (JP) .......................... 2001-210060

(51) Int. Cl.[7] .......................... G02B 26/00; G09G 3/34; C12P 7/62; G03G 74/04; A61K 9/50

(52) U.S. Cl. .......................... 359/296; 345/107; 435/135; 435/190; 435/320.1; 430/35; 430/108.1; 424/497; 428/138; 428/407

(58) Field of Search .......................... 359/296; 345/107; 435/135, 123, 190, 320.1, 325, 35, 108.1, 108.4, 108.22, 124, 137.1; 424/497, 489, 405; 428/138, 402.24, 407; 430/35, 108.1, 108.4, 108.22, 124, 137.1

(56) References Cited

U.S. PATENT DOCUMENTS

| | | | | |
|---|---|---|---|---|
| 5,004,664 A | * | 4/1991 | Fuller et al. | 430/109.4 |
| 6,027,787 A | * | 2/2000 | Noda | 428/138 |
| 6,117,658 A | * | 9/2000 | Dennis et al. | 435/135 |
| 6,146,665 A | * | 11/2000 | Marchessault et al. | 424/497 |
| 6,204,341 B1 | * | 3/2001 | Asrar et al. | 525/437 |
| 6,245,537 B1 | * | 6/2001 | Williams et al. | 435/135 |
| 6,485,951 B2 | * | 11/2002 | Yano et al. | 435/190 |
| 6,495,152 B2 | * | 12/2002 | Steinbuchel et al. | 424/405 |
| 6,576,450 B2 | * | 6/2003 | Skraly et al. | 435/135 |
| 6,593,116 B1 | * | 7/2003 | Huisman et al. | 435/135 |
| 6,600,029 B1 | * | 7/2003 | Sherman et al. | 536/23.2 |

FOREIGN PATENT DOCUMENTS

| | | |
|---|---|---|
| EP | 0 861 880 | 9/1998 |
| EP | 0 962 808 | 12/1999 |
| EP | 1 256 606 | 11/2002 |
| EP | 1 275 728 | 1/2003 |
| JP | 48-31097 | 4/1973 |
| JP | 21889525 | 7/1990 |
| JP | 2284128 | 11/1990 |
| JP | 05-173193 | 7/1993 |
| JP | 9-211499 | 8/1997 |
| JP | 2001-78753 | 3/2001 |
| JP | 2001-069968 | 3/2001 |

OTHER PUBLICATIONS

Y. L. Sang, "Plastic Bacteria? Progress And Prospects For Polyhydroxyalkanoate Production In Bacteria", TIBTECH, vol. 14, No. 11 (1996), pp. 431–437.

(List continued on next page.)

Primary Examiner—Loha Ben
(74) Attorney, Agent, or Firm—Fitzpatrick, Cella, Harper & Scinto

(57) ABSTRACT

Electrophoretic particles for electrophoretic display having excellent dispersibility and dispersion stability with time for insulating media, and being protected against coagulation, settling and the like, a process for production of the electrophoretic particles having high versatility for pigments to be used in response to a full-color display, and an electrophoretic display device using the electrophoretic particles that has an excellent memory property and is highly reliable are provided. The electrophoretic particles are formed using as at least a part of structure a pigment with at least a part of the surface covered with polyhydroxyalkanoate.

54 Claims, 5 Drawing Sheets

OTHER PUBLICATIONS

A. Steinbuchel et al., "Diversity of Bacterial Polyhydroxyalkanoic Acids", FEMS Microbiology Letters, vol. 128, No. 3 (1995), pp. 219–228.

Rehm, et al. "A New Metabolic Link...Synthesis"; J. Biol. Chem; 273, 37 (1998) 24044–24051.

Vogel, et al.; "Acetylornithinase of *E. Coli*; Partial Purification and Some Properties"; J. Biol. Chem., 218, 97–106 (1956).

Speier, et al.; "The Addition of Silicon Hydrides to Oleformic Double Bonds. Part I. The Use of Phenylsilane, Diphenylsilane, Phenylmethylsilane, Amylsilane and Tribromosilane"; J.A.C.S., 78, 2278 (1956).

Yamaguchi, et al.; "Oxidation of ω-(Benzoyloxy) alkanols with an Oxoaminium Salt"; J. Org. Chem. 1990, 55; 1490–1492.

Fritzsche, et al.; "Production of unsaturated polyesters by *Pseudomonas oleovorans*"; Int. J. Macromol; 1990, 12, 85–91.

Gerngross, et al.; "Enzyme–catalyzed synthesis of poly [(R)–(–)–3–hydroxybutyrate]: Formation of macroscopic granules in vitro"; Prac. Natl. Acad. Sci. USA, 92, 6279–6283, 1995.

Yamaguchi, et al.; "Kinetics of Depolarization–Induced Calcium Release from Skeletal Muscle Triads *In Vitro*"; J. Biochem. 121, 432–439 (1997).

Jossek, et al.; "In vitro synthesis of poly(3–hydroxybutyric acid) by using and enzymatic coenzyme A recycling system"; FEMS Microbiology Letters; 168 (1998) 319–324.

Lenz, et al; "Extracellular polymerization of 3–hydroxyalkanoate monomers with the polymerase of *Alcaligenes eutrophus*"; International Journal of Bilogical Macromolecules 25, (1999) 55–60.

Nobes, et al; "Growth and Kinetics of in vitro poly [R]–(–)3–hydroxybutyrate) granules interpreted as particulate polymerization with coalescene"; Macromol. Rapid Commun. 21 77–84 (2000).

Steinbrüchel, et al.; "In Vitro synthesis of poly (3–hydroxydeconoate): purification and enzymatic characterization of type II polyhydroxyalkanoate synthases PhaC1 and PhaC2 from *Pseudomonas aeruginosa*"; Appl. Microbiol. Biotechnol. (200) 54:37–43.

Pelletier, et al.; "2–Hydroxycyclohexanecarboreyl Coenzyme A Dehydrogenase, an Enzyme Characteristic of the Anaerobic Benzoate Degradation Pathway Used by *Rhodopseudomonas palustris*"; J. Bact., 182, 10, 2753–2760 (2000).

* cited by examiner

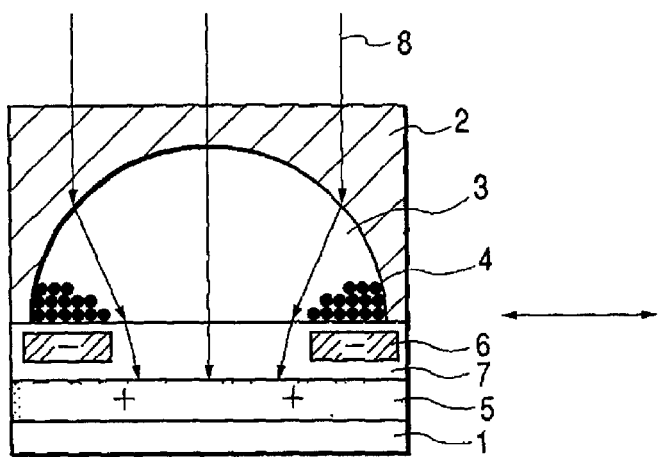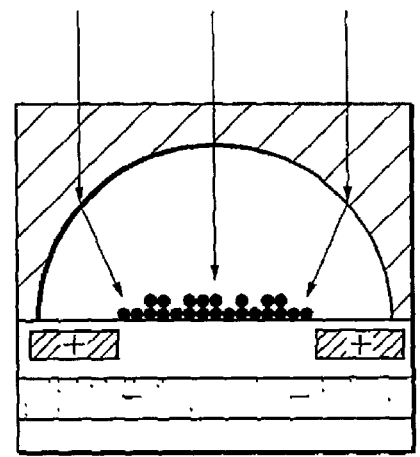

SEQUENCE LISTING

<160> NUMBER OF SEQ ID NOS: 14

<210> SEQ ID NO 1
<211> LENGTH: 559
<212> TYPE: PRT
<213> ORGANISM: Pseudomonas cichorii YN2; FERM BP-7375

<400> SEQUENCE: 1

```
Met Ser Asn Lys Ser Asn Asp Glu Leu Lys Tyr Gln Ala Ser Glu Asn
 1               5                   10                  15

Thr Leu Gly Leu Asn Pro Val Val Gly Leu Arg Gly Lys Asp Leu Leu
            20                  25                  30

Ala Ser Ala Arg Met Val Leu Arg Gln Ala Ile Lys Gln Pro Val His
        35                  40                  45

Ser Val Lys His Val Ala His Phe Gly Leu Glu Leu Lys Asn Val Leu
    50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95
```

-continued

```
Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
                245                 250                 255

Asn Pro Thr Lys Glu Gln Arg Glu Trp Gly Leu Ser Thr Tyr Ile Glu
            260                 265                 270

Ala Leu Lys Glu Ala Val Asp Val Val Thr Ala Ile Thr Gly Ser Lys
        275                 280                 285

Asp Val Asn Met Leu Gly Ala Cys Ser Gly Gly Ile Thr Cys Thr Ala
    290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
                325                 330                 335

Leu Phe Val Asn Glu Gln Thr Leu Glu Ala Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
                405                 410                 415

Lys Asn Asn Pro Leu Ile Arg Pro Asn Ala Leu Glu Val Cys Gly Thr
            420                 425                 430

Pro Ile Asp Leu Lys Gln Val Thr Ala Asp Ile Phe Ser Leu Ala Gly
        435                 440                 445

Thr Asn Asp His Ile Thr Pro Trp Lys Ser Cys Tyr Lys Ser Ala Gln
    450                 455                 460

Leu Phe Gly Gly Asn Val Glu Phe Val Leu Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Glu Val Ala Glu Asn Ala Asp Glu Trp Gln Ala Asn Ala Thr
            500                 505                 510
```

```
Lys His Thr Asp Ser Trp Trp Leu His Trp Gln Ala Trp Gln Ala Gln
        515                 520                 525

Arg Ser Gly Glu Leu Lys Lys Ser Pro Thr Lys Leu Gly Ser Lys Ala
        530                 535                 540

Tyr Pro Ala Gly Glu Ala Ala Pro Gly Thr Tyr Val His Glu Arg
545                 550                 555

<210> SEQ ID NO 2
<211> LENGTH: 1680
<212> TYPE: DNA
<213> ORGANISM: Pseudomonas cichorii YN2; FERM BP-7375

<400> SEQUENCE: 2
atgagtaaca agagtaacga tgagttgaag tatcaagcct ctgaaaacac cttggggctt      60
aatcctgtcg ttgggctgcg tggaaaggat ctactggctt ctgctcgaat ggtgcttagg     120
caggccatca agcaaccggt gcacagcgtc aaacatgtcg cgcactttgg tcttgaactc     180
aagaacgtac tgctgggtaa atccgggctg caaccgacca gcgatgaccg tcgcttcgcc     240
gatccggcct ggagccagaa cccgctctat aaacgttatt tgcaaaccta cctggcgtgg     300
cgcaaggaac tccacgactg gatcgatgaa agtaacctcg cccccaagga tgtggcgcgt     360
gggcacttcg tgatcaacct catgaccgaa gccatggcgc cgaccaacac gcgcgccaac     420
ccggcggcag tcaaacgctt tttcgaaacc ggtggcaaaa gcctgctcga cggcctctcg     480
cacctggcca aggatctggt acacaacggc ggcatgccga ccaggtcaa catgggtgca      540
ttcgaggtcg gcaagagcct gggcgtgacc gaaggcgcgg tggtgtttcg caacgatgtg     600
ctggaactga tccagtacaa gccgaccacc gagcaggtat acgaacgccc gctgctggtg     660
gtgccgccgc agatcaacaa gttctacgtt ttcgacctga gcccggacaa gagcctggcg     720
cggttctgcc tgcgcaacaa cgtgcaaacg ttcatcgtca gctggcgaaa tcccaccaag     780
gaacagcgag agtggggcct gtcgacctac atcgaagccc tcaaggaagc ggttgatgtc     840
gttaccgcga tcaccggcag caaagacgtg aacatgctcg gcgcctgctc cggcggcatc     900
acttgcaccg cgctgctggg ccattacgcg gcgattggcg aaaacaaggt caacgccctg     960
accttgctgg tgagcgtgct tgataccacc ctcgacagcg atgttgccct gttcgtcaat    1020
gaacagaccc ttgaagccgc caagcgccac tcgtaccagg ccggcgtact ggaaggccgc    1080
gacatggcga aggtcttcgc ctggatgcgc cccaacgatc tgatctggaa ctactgggtc    1140
aacaattacc tgctaggcaa cgaaccgccg gtgttcgaca tcctgttctg gaacaacgac    1200
accacacggt tgcccgcggc gttccacggc gacctgatcg aactgttcaa aaataaccca    1260
ctgattcgcc cgaatgcact ggaagtgtgc ggcaccccca tcgacctcaa gcaggtgacg    1320
gccgacatct tttccctggc cggcaccaac gaccacatca ccccgtggaa gtcctgctac    1380
aagtcggcgc aactgtttgg cggcaacgtt gaattcgtgc tgtcgagcag cgggcatatc    1440
cagagcatcc tgaacccgcc gggcaatccg aaatcgcgct acatgaccag caccgaagtg    1500
gcggaaaatg ccgatgaatg caagcgaat gccaccaagc ataccgattc ctggtggctg    1560
cactggcagg cctggcaggc ccaacgctcg ggcgagctga aaagtcccc gacaaaactg     1620
ggcagcaagg cgtatccggc aggtgaagcg gcgccaggca cgtacgtgca cgaacggtaa    1680

<210> SEQ ID NO 3
<211> LENGTH: 560
<212> TYPE: PRT
<213> ORGANISM: Pseudomonas cichorii YN2; FERM BP-7375
```

```
<400> SEQUENCE: 3

Met Arg Asp Lys Pro Ala Arg Glu Ser Leu Pro Thr Pro Ala Lys Phe
  1               5                  10                  15

Ile Asn Ala Gln Ser Ala Ile Thr Gly Leu Arg Gly Arg Asp Leu Val
             20                  25                  30

Ser Thr Leu Arg Ser Val Ala Ala His Gly Leu Arg His Pro Val His
         35                  40                  45

Thr Ala Arg His Ala Leu Lys Leu Gly Gly Gln Leu Gly Arg Val Leu
     50                  55                  60

Leu Gly Asp Thr Leu His Pro Thr Asn Pro Gln Asp Arg Arg Phe Asp
 65                  70                  75                  80

Asp Pro Ala Trp Ser Leu Asn Pro Phe Tyr Arg Arg Ser Leu Gln Ala
                 85                  90                  95

Tyr Leu Ser Trp Gln Lys Gln Val Lys Ser Trp Ile Asp Glu Ser Asn
            100                 105                 110

Met Ser Pro Asp Asp Arg Ala Arg Ala His Phe Ala Phe Ala Leu Leu
        115                 120                 125

Asn Asp Ala Val Ser Pro Ser Asn Ser Leu Leu Asn Pro Leu Ala Ile
130                 135                 140

Lys Glu Ile Phe Asn Ser Gly Gly Asn Ser Leu Val Arg Gly Ile Gly
145                 150                 155                 160

His Leu Val Asp Asp Leu Leu His Asn Asp Gly Leu Pro Arg Gln Val
                165                 170                 175

Thr Arg His Ala Phe Glu Val Gly Lys Thr Val Ala Thr Thr Thr Gly
            180                 185                 190

Ala Val Val Phe Arg Asn Glu Leu Leu Glu Leu Ile Gln Tyr Lys Pro
        195                 200                 205

Met Ser Glu Lys Gln Tyr Ser Lys Pro Leu Leu Val Val Pro Pro Gln
210                 215                 220

Ile Asn Lys Tyr Tyr Ile Phe Asp Leu Ser Pro His Asn Ser Phe Val
225                 230                 235                 240

Gln Phe Ala Leu Lys Asn Gly Leu Gln Thr Phe Val Ile Ser Trp Arg
                245                 250                 255

Asn Pro Asp Val Arg His Arg Glu Trp Gly Leu Ser Thr Tyr Val Glu
            260                 265                 270

Ala Val Glu Glu Ala Met Asn Val Cys Arg Ala Ile Thr Gly Ala Arg
        275                 280                 285

Glu Val Asn Leu Met Gly Ala Cys Ala Gly Gly Leu Thr Ile Ala Ala
    290                 295                 300

Leu Gln Gly His Leu Gln Ala Lys Arg Gln Leu Arg Arg Val Ser Ser
305                 310                 315                 320

Ala Thr Tyr Leu Val Ser Leu Leu Asp Ser Gln Leu Asp Ser Pro Ala
                325                 330                 335

Thr Leu Phe Ala Asp Glu Gln Thr Leu Glu Ala Ala Lys Arg Arg Ser
            340                 345                 350

Tyr Gln Lys Gly Val Leu Glu Gly Arg Asp Met Ala Lys Val Phe Ala
        355                 360                 365

Trp Met Arg Pro Asn Asp Leu Ile Trp Ser Tyr Phe Val Asn Asn Tyr
    370                 375                 380

Leu Met Gly Lys Glu Pro Pro Ala Phe Asp Ile Leu Tyr Trp Asn Asn
385                 390                 395                 400

Asp Asn Thr Arg Leu Pro Ala Ala Leu His Gly Asp Leu Leu Asp Phe
                405                 410                 415
```

```
Phe Lys His Asn Pro Leu Ser His Pro Gly Gly Leu Glu Val Cys Gly
            420                 425                 430

Thr Pro Ile Asp Leu Gln Lys Val Thr Val Asp Ser Phe Ser Val Ala
            435                 440                 445

Gly Ile Asn Asp His Ile Thr Pro Trp Asp Ala Val Tyr Arg Ser Thr
            450                 455                 460

Leu Leu Leu Gly Glu Arg Arg Phe Val Leu Ala Asn Ser Gly His
465                 470                 475                 480

Val Gln Ser Ile Leu Asn Pro Pro Asn Pro Lys Ala Asn Tyr Leu
                485                 490                 495

Glu Gly Ala Lys Leu Ser Ser Asp Pro Arg Ala Trp Tyr Tyr Asp Ala
            500                 505                 510

Lys Pro Val Asp Gly Ser Trp Trp Thr Gln Trp Leu Gly Trp Ile Gln
            515                 520                 525

Glu Arg Ser Gly Ala Gln Lys Glu Thr His Met Ala Leu Gly Asn Gln
            530                 535                 540

Asn Tyr Pro Pro Met Glu Ala Ala Pro Gly Thr Tyr Val Arg Val Arg
545                 550                 555                 560
```

<210> SEQ ID NO 4
<211> LENGTH: 1683
<212> TYPE: DNA
<213> ORGANISM: Pseudomonas cichorii YN2; FERM BP-7375

<400> SEQUENCE: 4

```
atgcgcgata aacctgcgag ggagtcacta cccaccccg ccaagttcat caacgcacaa    60
agtgcgatta ccggcctgcg tggccgggat ctggtttcga cttttgcgcag tgtcgccgcc   120
catggcctgc gccaccccgt gcacaccgcg cgacacgcct tgaaactggg tggtcaactg   180
ggacgcgtgt tgctgggcga caccctgcat cccaccaacc cgcaagaccg tcgcttcgac   240
gatccggcgt ggagtctcaa tccctttat cgtcgcagcc tgcaggcgta cctgagctgg   300
cagaagcagg tcaagagctg gatcgacgaa agcaacatga gcccggatga ccgcgcccgt   360
gcgcacttcg cgttcgccct gctcaacgat gccgtgtcgc cgtccaacag cctgctcaat   420
ccgctggcga tcaaggaaat cttcaactcc ggcggcaaca gcctggtgcg cgggatcggc   480
catctggtcg atgacctctt gcacaacgat ggcttgcccc ggcaagtcac caggcatgca   540
ttcgaggttg gcaagaccgt cgccaccacc accggcgccg tggtgtttcg caacgagctg   600
ctggagctga tccaatacaa gccgatgagc gaaaagcagt attccaaacc gctgctggtg   660
gtgccgccac agatcaacaa gtactacatt tttgacctca gcccccataa cagcttcgtc   720
cagttcgcgc tcaagaacgg cctgcaaacc ttcgtcatca gctggcgcaa tccggatgta   780
cgtcaccgcg aatgggggcct gtcgacctac gtcgaagcgg tggaagaagc catgaatgtc   840
tgccgggcaa tcaccggcgc gcgcgaggtc aacctgatgg cgcctgcgc tggcgggctg   900
accattgctg ccctgcaggg ccacttgcaa gccaagcgac agctgcgccg cgtctccagc   960
gcgacgtacc tggtgagcct gctcgacagc caactggaca gcccggccac actcttcgcc  1020
gacgaacaga ccctggaggc ggccaagcgc cgctcctacc agaaaggtgt gctggaaggc  1080
cgcgacatgg ccaaggtttt cgcctggatg cgccccaacg atttgatctg gagctacttc  1140
gtcaacaatt acctgatggg caaggagccg ccggcgttcg acattctcta ctggaacaat  1200
gacaacacac gcctgccggc cgccctgcat ggtgacttgc tggacttctt caagcacaac  1260
ccgctgagcc atccgggtgg cctggaagtg tgcggcaccc cgatcgactt gcaaaaggtc  1320
```

```
accgtcgaca gtttcagcgt ggccggcatc aacgatcaca tcacgccgtg ggacgcggtg    1380
tatcgctcaa ccctgttgct cggtggcgag cgtcgctttg tcctggccaa cagcggtcat    1440
gtgcagagca ttctcaaccc gccgaacaat ccgaaagcca actacctcga aggtgcaaaa    1500
ctaagcagcg accccagggc ctggtactac gacgccaagc ccgtcgacgg tagctggtgg    1560
acgcaatggc tgggctggat tcaggagcgc tcgggcgcgc aaaaagaaac ccacatggcc    1620
ctcggcaatc agaattatcc accgatggag gcggcgcccg ggacttacgt gcgcgtgcgc    1680
tga                                                                  1683
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 5
tgctggaact gatccagtac                                                 20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 6
gggttgagga tgctctggat gtg                                             23

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 7
ggaccaagct tctcgtctca gggcaatgg                                       29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 8
cgagcaagct tgctcctaca ggtgaaggc                                       29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 9
gtattaagct tgaagacgaa ggagtgttg                                       29

```
<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 10
catccaagct tcttatgatc gggtcatgcc                                          30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 11
cgggatccag taacaagagt aacgatgagt                                          30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 12
cgatctcgag ttaccgttcg tgcacgtacg                                          30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 13
cgggatcccg cgataaacct gcgagggagt                                          30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 14 cgag gcgcacgcgc acgtaagtcc                                                30
```

PARTICLES FOR ELECTROPHORESIS, A PRODUCTION METHOD THEREOF AND A DISPLAY USING THE PARTICLES

BACKGROUND OF THE INVENTION

1. Field of the Invention

The present invention relates to electrophoretic particles for use in an electrophoretic display apparatus utilizing charged particles in a medium being moved by application of a voltage, a process for production of the electrophoretic particles, and an electrophoretic display device using the electrophoretic particles.

2. Related Background Art

The electrophoretic phenomenon is a phenomenon in which when certain particles are suspended in a medium (dispersing medium), the particles are electrically charged, and when an electric field is applied to the charged particles, they move (make a migration) through the dispersion medium to an electrode having an opposite charge. Electrophoretic particles for use in an electrophoretic display apparatus using such a phenomenon include, for example, inorganic pigments such as titanium oxide, zinc oxide, zirconium oxide, iron oxide, aluminum oxide, cadmium selenide, carbon black, barium sulfate, lead chromate, zinc sulfide and cadmium sulfide, and organic pigments such as phthalocyanine blue, phthalocyanine green, Hansa yellow, Watching red and Dialyride yellow. For conventional electrophoretic particles, however, there have been cases where electrophoretic particles dispersed in the dispersion medium coagulate together, or electrophoretic particles gradually settle out over time due to a difference in specific gravity between the electrophoretic particle and the dispersion medium, or the electrophoretic particle is not charged enough to make a response to application of a voltage sufficiently, and a phenomenon of irreversible adsorption to an electrode plate occurs.

In order to solve these problems, it has been proposed that the specific gravity of the electrophoretic particle is made substantially equal to that of the dispersion medium by covering the electrophoretic particle with resin (Japanese Patent Application Laid-Open No. 48-31097).

In addition, it has been proposed that small particles of titanium dioxide as electrophoretic particles are covered with silicon resin, thereby giving a large amount of spontaneous charge to the electrophoretic particles, and these electrophoretic particles are used in an electrophoretic device with dyes coexisting in the dispersion medium (Japanese Patent Application Laid-Open No. 02-189525). In addition, it has been proposed that small particles of titanium dioxide as electrophoretic particles are covered with polyethylene resin, thereby giving a large amount of spontaneous charge to the electrophoretic particles, and these electrophoretic particles are used in an electrophoretic device with dyes coexisting in the dispersion medium (Japanese Patent Application Laid-Open No. 09-211499). In addition, it has been proposed that electrophoretic particles are treated with a titanate based coupling agent and sorbitan fatty ester (Japanese Patent Application Laid-Open No. 02-284128).

In addition, it has been proposed that an functional group is introduced on the surface of the electrophoretic particle, and this functional group is subjected to a graft reaction with a polymer, thereby modifying the surface of the electrophoretic particle (Japanese Patent Application Laid-Open No. 05-173193).

The electrophoretic particle covered with the above described silicon resin or polyethylene resin has a specific gravity substantially equal to the dispersion medium, thus making it possible to prevent the settling of electrophoretic particles in the dispersion medium and to increase the amount of charge, but it is necessary to disperse electrophoretic particles in a heated and dissolved resin and finely grind the electrophoretic particles to sizes suitable for the electrophoretic display device after they are cooled and cured in their production process, thus bringing about a disadvantage that enormous amounts of energy and time are required. Also, in the electrophoretic device with dyes coexisting in the dispersion medium, there is a disadvantage that the resin with which electrophoretic particles are covered tends to be smeared with dyes and the like in the dispersion medium, and therefore a contrast between the electrophoretic particle and the dispersion medium may be reduced.

In addition, introduction of a functional group on the surface of the electrophoretic particle to treat the electrophoretic particle with a titanate based coupling agent and sorbitan fatty ester, and graft reaction of the electrophoretic particle with a polymer are effective measures for surface modification, but these measures have a disadvantage that functional groups that can be introduced depending on a pigment to be used are limited, and introduction of functional groups on the surface depending on a variety of pigments may be complicated and lacking in general versatility.

The present invention has been made in view of these circumstances, and its object is to provide electrophoretic particles for electrophoretic display having excellent dispersibility and dispersion stability with time for an insulating medium and prevented from coagulating and settling out, a process for production of the electrophoretic particles that is versatile for pigments to be used in order to correspond to a full-color display, and an electrophoretic display device using the electrophoretic particles that has an excellent memory property and is highly reliable.

SUMMARY OF THE INVENTION

As a result of vigorous studies conducted by the inventors in order to solve the above problems, it has been found that it is possible for the pigment to be contained in a fine microcapsule easily without using a surfactant by fixing a polyhydroxyalkanoate (hereinafter referred to as PHA if abbreviated) synthetizing enzyme to a pigment dispersed in an aqueous medium and adding 3-hydroxyacyl coenzyme A thereto to carry out a reaction, and at this time, the pigment is contained in high density because the surface of the pigment is covered directly with the PHA, and selection of an appropriate type of 3-hydroxyacyl coenzyme A allows a large amount of spontaneous charge to be given to the micro-capsulated pigment covered with the PHA. In addition, it has been found that a micro-capsulated pigment with various kinds of properties and the like improved can be obtained by subjecting the PHA to chemical modification. Further specifically, it has been found that by introducing a graft chain into the PHA, for example, it is possible to obtain a micro-capsulated pigment with at least part of the pigment covered by PHA having various kinds of properties derived from the graft chain. In addition, it has been found that by cross-linking the PHA, it is possible to obtain a micro-capsulated pigment with at least part of the pigment covered with PHA having desired physicochemical properties (e.g. mechanical strength, chemical resistance, heat resistance, etc.). Furthermore, the term "chemical modification" in the present invention means carrying out an intramolecular or intermolecular chemical reaction of a polymer material, or carrying out a chemical reaction between a polymer material and another chemical to modify the molecular structure of the polymer material. The term "crosslinking" means chemically or physicochemically making an intramolecular or intermolecular linkage of a polymer material to form a network structure, and the term "crosslinking agent" means a substance having certain reactivity with the above described polymer material that is added for carrying out the above described crosslinking reaction.

In addition, it has been found that the composition of PHA is selected as appropriate, whereby the micro-capsulated pigment can be made to have excellent dispersibility and dispersion stability with time in the insulating medium as electrophoretic particles, leading to completion of the present invention.

According to an aspect of the present invention, there is provided an electrophoretic particle comprising a pigment at least a part of the surface of which pigment is covered with polyhydroxyalkanoate.

According to another aspect of the present invention, there is provided a process for preparing of electrophoretic particles, comprising the step of carrying out a polyhydroxyalkanoate synthesis reaction with 3-hydroxyacyl CoA as a substrate in the presence of a polyhydroxyalkanoate synthesizing enzyme fixed on the surfaces of the pigment particles dispersed in the aqueous medium, thereby at least part of the surface of the pigment particle is coverd with polyhydroxyalkanoate to obtain electrophoretic particles.

According to still another aspect of the present invention, there is provided an electrophoretic display device having a structure in which a dispersion system of the above described electrophoretic particles is enclosed in a space formed by placing a pair of electrode plates at a predetermined interval, and control means for applying a controlling voltage to between the above described electrode plates to change the state of distribution of electrophoretic particles in the above described dispersion system is provided.

The electrophoretic particle in the present invention has a structure in which at least part of the surface of the pigment particle is covered with polyhydroxyalkanoate, and it is not necessarily required that the entire surface of the pigment particle be covered as long as desired properties of electrophoretic particles can be obtained. In a state in which the entire surface is covered, a micro-capsulated pigment as electrophoretic particles with the pigment particle as a core and with a cover of polyhydroxyalkanoate as a shell can be obtained.

BRIEF DESCRIPTION OF THE DRAWINGS

FIGS. 1A and 1B are sectional views of a display apparatus of the present invention;

DESCRIPTION OF THE PREFERRED EMBODIMENTS

Figure 2A:
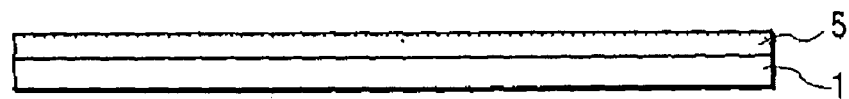
FIGS. 2A, 2B, 2C and 2D are flow sheets for production of an electrophoretic display device.

The present invention will be described more in detail below.

<PHA>

PHA capable of being used in the present invention is not particularly limited as long as such a PHA can be synthesized with a PHA synthesizing enzyme involved in a biosynthesis reaction of PHA.

Here, the biosynthesis of PHA is carried out through a polymerization reaction by an enzyme using as a substrate (R)-3-hydroxyacyl CoA produced from alkanoic acids as a substrate by way of various metabolic pathways in an organism (e.g. β-oxidation system and fatty acid synthesis pathway). It is a PHA synthesizing enzyme (also referred to as PHA polymerase, PHA synthase) that catalyses this polymerization reaction. The term "CoA" is an abbreviation of coenzyme A, of which chemical structure is as follows:

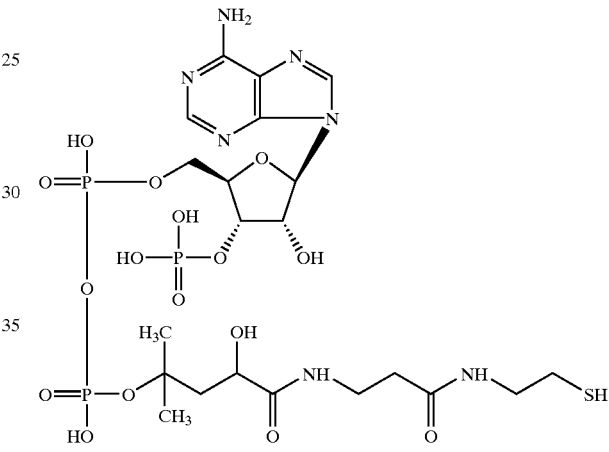

A reaction by which PHA is produced from alkanoic acid through a polymerization reaction by a β-oxidation system and a PHA synthesizing enzyme is shown in the following:

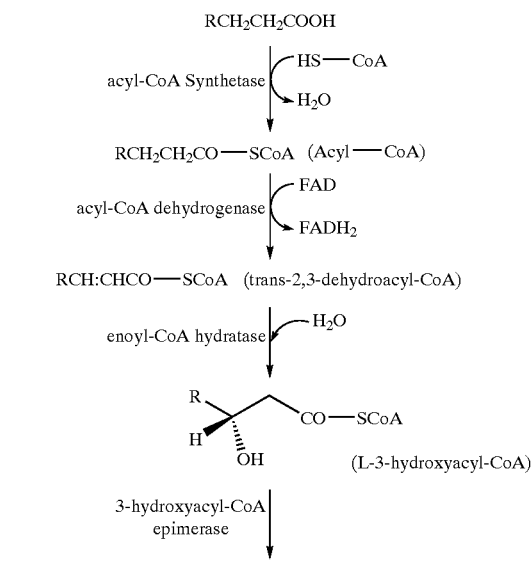

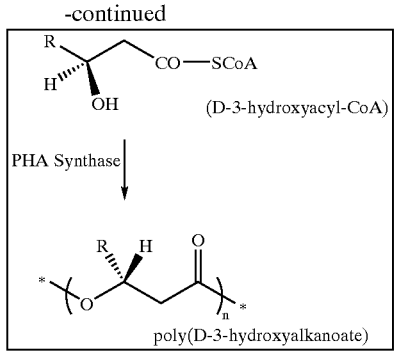

On the other hand, if the reaction is carried out by way of the fatty acid synthesis pathway, it can be considered that PHA is similarly synthesized by the PHA synthesizing enzyme using as a substrate (R)-3-hydroxyacyl CoA into which (R)-3-hydroxyacyl-ACP (ACP means an acyl carrier protein) produced in the pathway has been converted.

In addition, it is known that the above described PHB synthesizing enzyme and PHA synthesizing enzyme can be taken out from the cell to synthesize PHA in a cell-free system (in vitro), and specific examples thereof will be described below.

For example, in Proc. Natl. Acad. Sci. USA, 92, 6279–6283 (1995), it is reported that PHB comprising a 3-hydroxy-n-butanoic acid unit has been successfully synthesized by making 3-hydroxybutyryl CoA act on a PHB synthesizing enzyme derived from *Alcaligenes eutrophus*. In addition, it is reported in Int. J. Biol. Macromol., 25, 55–60 (1999) that PHA comprising a 3-hydroxy-n-butyryl acid unit or a 3-hydroxy-n-valeric acid unit has been successfully synthesized by making 3-hydroxybutyryl CoA and 3-hydroxyvaleryl CoA act on the PHB synthesizing enzyme derived from *Alcaligenes eutrophus*. In addition, according to this report, when racemic 3-hydroxybutyryl CoA was made to act on the enzyme, PHB comprising only a 3-hydroxy-n-butyric acid unit of R-configuration was synthesized due to the stereoselectivity of the enzyme. Synthesis of PHB outside the cell using a PHB synthesizing enzyme derived from *Alcaligenes eutrophus* is also reported in Macromol. Rapid Commun., 21, 77–84 (2000). In addition, it is reported in FEMS Microbiol. Lett., 168, 319–324 (1998) that PHB comprising a 3-hydroxy-n-butyric unit has been successfully synthesized by making 3-hydrozybutyryl CoA act on a PHB synthesizing enzyme derived from *Chromatium vinosum*. It is reported in Appl. Microbiol. Biotechnol., 54, 37–43 (2000) that PHA comprising a 3-hydroxydecanoic acid unit has been synthesized by making 3-hydroxydecanoyl CoA act on a PHA synthesizing enzyme from *Pseudomonas aeruginosa*.

In this way, the PHA synthesizing enzyme is an enzyme catalyzing a final stage in the PHA synthesis reaction system in an organism, and any PHA known to be capable of being synthesized in the organism is synthesized under catalytic action by the enzyme. Therefore, by making 3-hydroxyacyl CoA corresponding to desired PHA act on the enzyme fixed on the medium in the present invention, micro-capsulated pigments with the pigments covered with any type of PHA known to be capable of being synthesized in the organism can be prepared.

As an example of PHA for use in the present invention, PHA containing at least monomer units expressed by the following formulas [1] to [10] can specifically be shown.

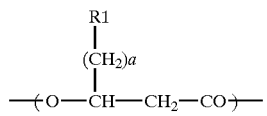

[1]

(wherein the monomer unit is at least one selected from the group consisting of monomer units having any of the following combinations of R1 and a:

a monomer unit in which R1 represents a hydrogen atom (H), and a represents an integer number of 0 to 10;

a monomer unit in which R1 represents a halogen atom, and a represents an integer number of 1 to 10;

a monomer unit in which R1 represents a chromophoric group, and a represents an integer number of 1 to 10;

a monomer unit in which R1 represents a carboxyl group or a salt thereof, and a represents an integer number of 1 to 10; and a monomer unit in which R1 represents

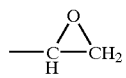

, and a represents an integer number of 1 to 7.)

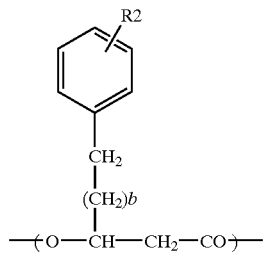

[2]

(wherein b represents an integer number of 0 to 7, and R2 represents any one selected from the group consisting of a hydrogen atom (H), halogen atom, —CN, —NO$_2$, —CF$_3$, —C$_2$F$_5$ and —C$_3$F$_7$.)

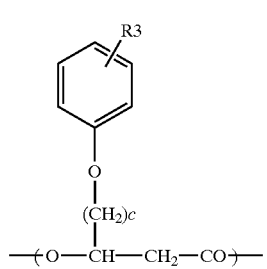

[3]

(wherein c represents an integer number of 1 to 8, and R3 represents any one selected from the group consisting of a hydrogen atom (H), halogen atom, —CN, —NO$_2$, —CF$_3$, —C$_2$F$_5$ and —C$_3$F$_7$.)

[4]

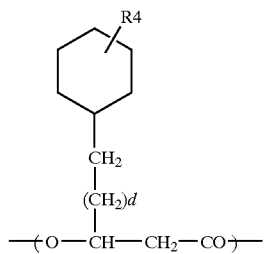

(wherein d represents an integer number of 0 to 7, and R4 represents any one selected from the group consisting of a hydrogen atom (H), halogen atom, —CN, —NO$_2$, —CF$_3$, —C$_2$F$_5$ and —C$_3$F$_7$.)

[5]

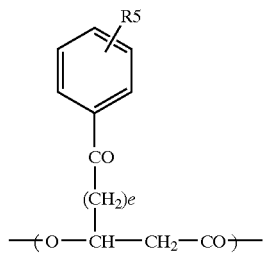

(wherein e represents an integer number of 1 to 8, and R5 represents any one selected from the group consisting of a hydrogen atom (H), halogen atom, —CN, —NO$_2$, —CF$_3$, —C$_2$F$_5$, —C$_3$F$_7$, —CH$_3$, —C$_2$H$_5$ and —C$_3$H$_7$).

[6]

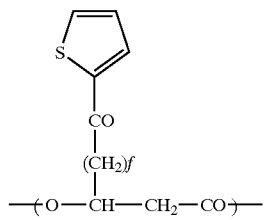

(wherein f represents an integer number of 0 to 7.)

[7]

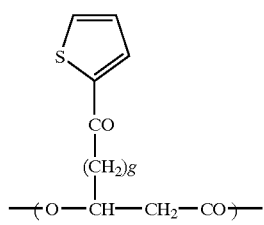

(wherein g represents an integer number of 1 to 8.)

[8]

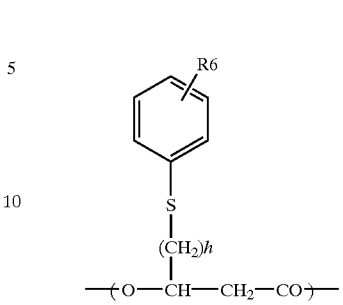

(wherein h represents an integer number of 1 to 7, R6 represents any one selected from the group consisting of a hydrogen atom (H), halogen atom, —CN, —NO$_2$, —COOR', —SO$_2$R", —CH$_3$, —C$_2$H$_5$, —C$_3$H$_7$, —CH(CH$_3$)$_2$ and —C(CH$_3$)$_3$ wherein R' represents any of a hydrogen atom (H), Na, K, —CH$_3$ and —C$_2$H$_5$, and R" represents any of —OH, —ONa, —OK, a halogen atom, —OCH$_3$ and —OC$_2$H$_5$.)

[9]

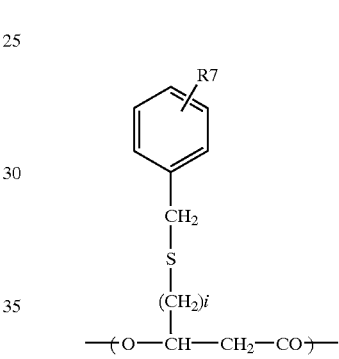

(wherein i represents an integer number of 1 to 7, R7 represents any one selected from the group consisting of a hydrogen atom (H), halogen atom, —CN, —NO$_2$, —COOR' and —SO$_2$R" wherein R' represents any of a hydrogen atom (H), Na, K, —CH$_3$ and —C$_2$H$_5$, and R" represents any of —OH, —ONa, —OK, a halogen atom, —OCH$_3$ and —OC$_2$H$_5$.)

[10]

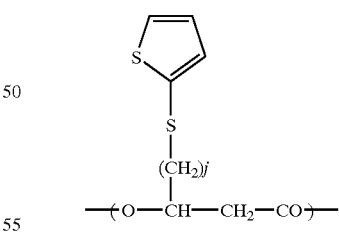

(wherein j represents an integer number of 1 to 9.)

Furthermore, examples of the above described halogen atom may include fluorine, chlorine and bromine.

The present invention is a process for production of electrophoretic particles in which the above described polyhydroxyalkanoate is polyhydroxyalkanoate including at least one selected from the group consisting of monomer units expressed by formulas [1] to [10], the above described each corresponding 3-hydroxyacyl coenzyme A is any of 3-hydroxyacyl coenzymes A expressed by Formulas [11] to [20].

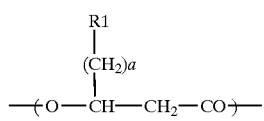

(wherein the monomer unit is at least one selected from the group consisting of monomer units having any of the following combinations of R1 and a:

- a monomer unit in which R1 represents a hydrogen atom (H), and a represents an integer number of 0 to 10;
- a monomer unit in which R1 represents a halogen atom, and a represents an integer number of 1 to 10;
- a monomer unit in which R1 represents a chromophoric group, and a represents an integer number of 1 to 10;
- a monomer unit in which R1 represents a carboxyl group or a salt thereof, and a represents an integer number of 1 to 10; and
- a monomer unit in which R1 represents

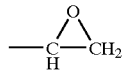

, and a represents an integer number of 1 to 7.)

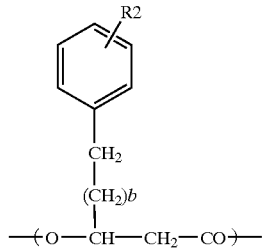

(wherein b represents an integer number of 0 to 7, and R2 represents any one selected from the group consisting of a hydrogen atom (H), halogen atom, —CN, —NO$_2$, —CF$_3$, —C$_2$F$_5$ and —C$_3$F$_7$.)

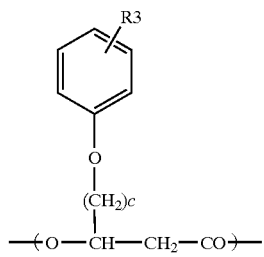

(wherein c represents an integer number of 1 to 8, and R3 represents any one selected from the group consisting of a hydrogen atom (H), halogen atom, —CN, —NO$_2$, —CF$_3$, —C$_2$F$_5$ and —C$_3$F$_7$.)

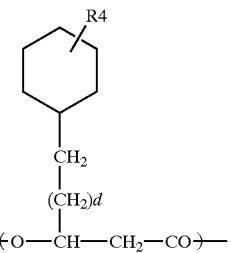

(wherein d represents an integer number of 0 to 7, and R4 represents any one selected from the group consisting of a hydrogen atom (H), halogen atom, —CN, —NO$_2$, —CF$_3$, —C$_2$F$_5$ and —C$_3$F$_7$.)

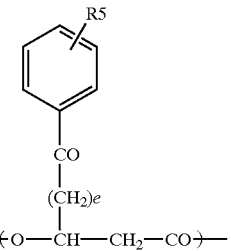

(wherein e represents an integer number of 1 to 8, and R5 represents any one selected from the group consisting of a hydrogen atom (H), halogen atom, —CN, —NO$_2$, —CF$_3$, —C$_2$F$_5$, —C$_3$F$_7$, —CH$_3$, —C$_2$H$_5$ and —C$_3$H$_7$).

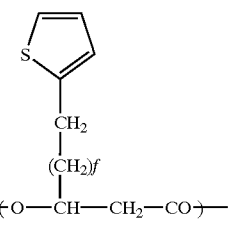

(wherein f represents an integer number of 0 to 7.)

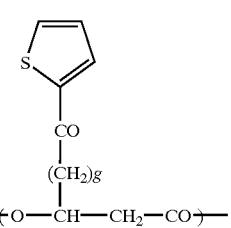

(wherein g represents an integer number of 1 to 8.)

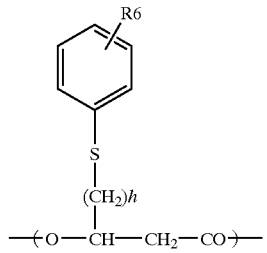

[8]

(wherein h represents an integer number of 1 to 7, R6 represents any one selected from the group consisting of a hydrogen atom (H), halogen atom, —CN, —NO$_2$, —COOR', —SO$_2$R", —CH$_3$, —C$_2$H$_5$, —C$_3$H$_7$, —CH(CH$_3$)$_2$ and —C(CH$_3$)$_3$ wherein R' represents any of a hydrogen atom (H), Na, K, —CH$_3$ and —C$_2$H$_5$, and R" represents any of —OH, —ONa, —OK, a halogen atom, —OCH$_3$ and —OC$_2$H$_5$.)

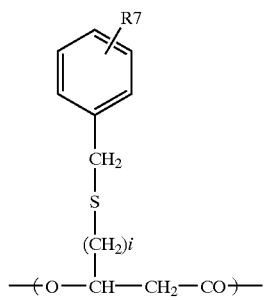

[9]

(wherein i represents an integer number of 1 to 7, R7 represents any one selected from the group consisting of a hydrogen atom (H), halogen atom, —CN, —NO$_2$, —COOR' and —SO$_2$R" wherein R' represents any of a hydrogen atom (H), Na, K, —CH$_3$ and —C$_2$H$_5$, and R" represents any of —OH, —ONa, —OK, a halogen atom, —OCH$_3$ and —OC$_2$H$_5$.)

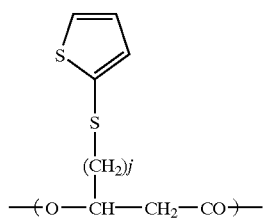

[10]

(wherein j represents an integer number of 1 to 9.)

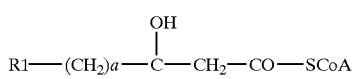

[11]

(wherein —SCoA represents a coenzyme A bound to alkanoic acid, and the combination of R1 and a is at least one selected from the group consisting of the following combinations, and corresponds to the R1 and a in the monomer unit expressed by the above described Formula [1]:

a monomer unit in which R1 represents a hydrogen atom (H), and a represents an integer number of 0 to 10;

a monomer unit in which R1 represents a halogen atom, and a represents an integer number of 1 to 10;

a monomer unit in which R1 represents a chromophoric group, and a represents an integer number of 1 to 10;

a monomer unit in which R1 represents a carboxyl group or a salt thereof, and a represents an integer number of 1 to 10; and a monomer unit in which R1 represents

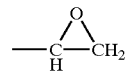

, and a represents an integer number of 1 to 7.)

[12]

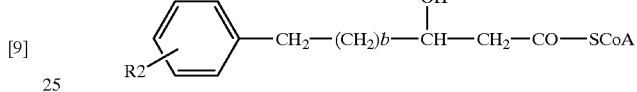

(wherein —SCoA represents a coenzyme A bound to alkanoic acid, b represents an integer number of 0 to 7 corresponding to b in the monomer unit expressed by the above described Formula [2], and R2 represents any one selected from the group consisting of a hydrogen atom (H), halogen atom, —CN, —NO$_2$, —CF$_3$, —C$_2$F$_5$ and —C$_3$F$_7$ corresponding to R2 in the monomer unit expressed by the above described Formula [2].)

[13]

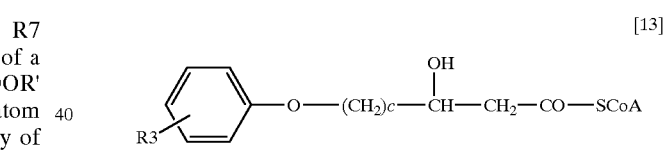

(wherein —SCoA represents a coenzyme A bound to alkanoic acid, c represents an integer number of 1 to 8 corresponding to c in the monomer unit expressed by the above described Formula [3], and R3 represents any one selected from the group consisting of a hydrogen atom (H), halogen atom, —CN, —NO$_2$, —CF$_3$, —C$_2$F$_5$ and —C$_3$F$_7$ corresponding to R3 in the monomer unit expressed by the above described Formula [3].)

[14]

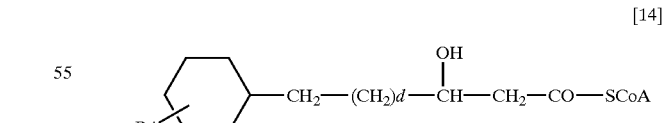

(wherein —SCoA represents a coenzyme A bound to alkanoic acid, d represents an integer number of 0 to 7 corresponding to d in the monomer unit expressed by the above described Formula [4], and R4 represents any one selected from the group consisting of a hydrogen atom (H), halogen atom, —CN, —NO$_2$, —CF$_3$, —C$_2$F$_5$ and —C$_3$F$_7$ corresponding to R4 in the monomer unit expressed by the above described Formula [4].)

[15]

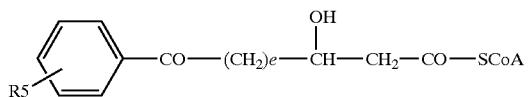

(wherein —SCoA represents a coenzyme A bound to alkanoic acid, e represents an integer number of 1 to 8 corresponding to e in the monomer unit expressed by the above described Formula [5], and R5 represents any one selected from the group consisting of a hydrogen atom (H), halogen atom, —CN, —$NO_2$, —$CF_3$, —$C_2F_5$, —$C_3F_7$, —$CH_3$, —$C_2H_5$ and —$C_3H_7$ corresponding to R5 in the monomer unit expressed by the above described Formula [5].)

[16]

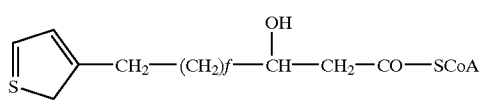

(wherein —SCoA represents a coenzyme A bound to alkanoic acid, and f represents an integer number of 0 to 7 corresponding to f in the monomer unit expressed by the above described Formula [6].)

[17]

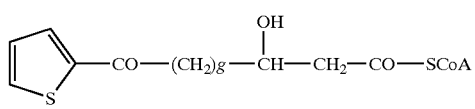

(wherein —SCoA represents a coenzyme A bound to alkanoic acid, and g represents an integer number of 1 to 8 corresponding to g in the monomer unit expressed by the above described Formula [7].)

[18]

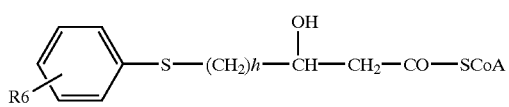

(wherein —SCoA represents a coenzyme A bound to alkanoic acid, h represents an integer number of 1 to 7 corresponding to h in the monomer unit expressed by the above described Formula [8], and R6 represents any one selected from the group consisting of a hydrogen atom (H), halogen atom, —CN, —$NO_2$, —COOR', —$SO_2R''$, —$CH_3$, —$C_2H_5$, —$C_3H_7$, —$CH(CH_3)_2$ and —$C(CH_3)_3$ corresponding to R6 in the monomer unit expressed by the above described Formula [8] wherein R' represents any of a hydrogen atom (H), Na, K, —$CH_3$ and —$C_2H_5$, and R'' represents any of —OH, —ONa, —OK, a halogen atom, —$OCH_3$ and —$OC_2H_5$.)

[19]

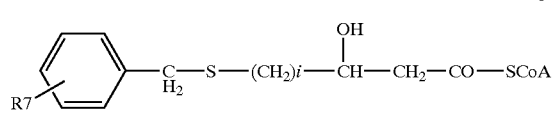

(wherein —SCoA represents a coenzyme A bound to alkanoic acid, i represents an integer number of 1 to 7 corresponding to i in the monomer unit expressed by the above described Formula [9], and R7 represents any one selected from the group consisting of a hydrogen atom (H), halogen atom, —CN, —$NO_2$, —COOR' and —$SO_2R''$ corresponding to R7 in the monomer unit expressed by the above described Formula [9] wherein R' represents any of a hydrogen atom (H), Na, K, —$CH_3$ and —$C_2H_5$, and R'' represents any of —OH, —ONa, —OK, a halogen atom, —$OCH_3$ and —$OC_2H_5$.)

[20]

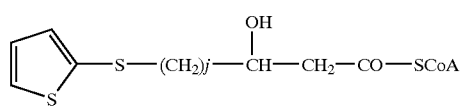

(wherein —SCoA represents a coenzyme A bound to alkanoic acid, and j represents an integer number of 1 to 9 corresponding to j in the monomer unit expressed by the above described Formula [10].)

Furthermore, specific examples of the above described halogen atom may include fluorine, chlorine and bromine. In addition, the above described chromophoric group is not particularly limited as long as its 3-hydroxyacyl CoA body can be subjected to catalytic action of the PHA synthesizing enzyme, but it is more desirable that a methylene chain having 1 to 5 carbon atoms exists between the carboxyl group with CoA bound thereto and the chromophoric group in the 3-hydroxyacyl CoA molecule if considering steric hindrance that may occur during synthesis of a polymer. In addition, if the optical absorption wavelength of the chromophoric group is in the visible range, a colored microcapsulated pigment can be obtained even if an extender pigment is used. Examples of such chromophoric groups may include nitroso, nitro, azo, diarylmethane, triarylmethane, xanthene, acridine, quinoline, methine, thiazole, indamine, indophenol, lactone, aminoketone, hydroxyketone, stilbene, azine, oxazine, thiazin, anthraquinone, phthalocyanine and indigoid.

For PHA to be used in the present invention, random copolymers and block copolymers each including the above described plurality of monomer units can also be used, thus making it possible to control properties of PHA and provide a plurality of functions using the properties of respective monomer units and contained functional groups, to realize new functions using interaction between functional groups, and so on. In addition, it is also possible to synthesize a block copolymer of any order and composition on the surface of the pigment by selecting as appropriate the amount and order in which 3-hydroxyacyl CoA as a substrate is added. In addition, as required, chemical modification and the like may also be made after or during synthesis of PHA.

It is also possible to change the composition of the monomer unit of PHA in the direction extending from the inside of the pigment to the outside thereof by changing with time the composition such as type and concentration of 3-hydroxyacyl CoA as a substrate, for example. Thereby, for example, if it is necessary to form a cover structure with PHA having a low affinity for the pigment, the substrate is first covered with PHA having a high affinity for the substrate, and the composition of the monomer unit of PHA having a high affinity for the pigment is changed to the composition of the monomer unit of desired PHA in the direction extending from the inside toward the outside, or in the vertical direction to form, for example, a multi-layer structure or gradient structure, thereby making it possible to form a PHA cover with its bonding to the pigment enhanced.

In addition, by introducing a graft chain in PHA on the surface of the micro-capsulated pigment, a micro-capsulated pigment having properties derived from the graft chain can be obtained. In addition, by having PHA on the surface of the pigment crosslinked, a micro-capsulated pigment having excellent mechanical strength can be obtained.

Furthermore, PHA synthesized by a PHA synthesizing enzyme, which is used in the structure of the present invention, is generally an isotactic polymer constituted only by a R-configuration.

3-hydroxyacyl CoA as a synthesis substrate for PHA can be synthesized for use by a method appropriately selected from an in vitro synthesis method using enzymes, an in vivo synthesis method using organisms such as microorganisms and plants, a chemical synthesis method, and the like. In particular, the enzyme synthesis method is a method that is generally used for synthesis of the substrate, and known enzyme synthesis methods include a method using the following reaction using commercially available acyl CoA synthetase (Acyl CoA Ligase, E.C.6.2.1.3)(Eur. J.Biochem., 250, 432–439 (1997), Appl. Microbiol. Biotechnol., 54, 37–43 (2000), etc.):

$$\text{3-hydroxyalkanoic acid} + \text{CoA} \xrightarrow{\text{acyl CoA synthetase}} \text{3-hydroxyacyl CoA}.$$

For the synthesis process using enzymes and organisms, a batch type synthesis method may be used, or series production may be carried out using immobilized enzymes and immobilized cells.

<PHA Synthesizing Enzymes and Microorganisms for Producing the Enzymes>

For the PHA synthesizing enzyme for use in the present invention, an enzyme produced by a microorganism appropriately selected from microorganisms capable of producing the enzyme, or a transformant with the gene of a PHA synthesizing enzyme introduced in a host microorganism may be used.

For microorganisms for producing PHA synthesizing enzymes, PHB or PHB/V producing microorganisms may be used, and as these microorganisms, *Burkholderia cepacia* KK01, *Ralstonia eutropha* TB64, *Alcaligenes* sp. TL2 that have been isolated by the inventors may be used in addition to *Aeromonas* sp., *Alcaligenes* sp., *Chromatium* sp., *Comamonas* sp., *Methylobacterium* sp., *Paracoccus* sp., *Pseudomonas* sp. and the like. Furthermore, KK01, TB64 and TL2 are deposited as FERM BP-4235, FERM BP-6933 and FERM BP-6913, respectively, in National Institute of Advanced Industrial Science and Technology, International Patent Organism Depositary.

Also, as microorganisms for producing PHA synthesizing enzymes, microorganisms producing mcl-PHA and unusual-PHA may be used, and as these microorganisms may be used *Pseudomonas* sp. microorganisms such as *Pseudomonas putida* P91, *Psuedomonas cichorii* H45, *Pseudomonas cichorii* YN2, *Pseudomonas jessenii* P161, etc. that have been isolated by the inventors, in addition to *Pseudomonas oleoborans, Pseudomonas resinoborans, Pseudomonas* sp. 61–3, *Pseudomonas putida* KT2442, *Pseudomonas aeruginosa* and the like, and *Burkholderia* sp. microorganisms such as *Burkholderia* sp. OK3 (FERM P-17370) described in Japanese Patent Application Laid-Open No. 2001-78753 and *Burkholderia* sp. OK4 (FERM P-17371) described in Japanese Patent Application Laid-Open No. 2001-69968. Also, in addition to these microorganisms, microorganisms belonging to *Aeromonas* sp., *Comamonas* sp. and the like and producing mcl-PHA and unusual-PHA can be used.

Furthermore, P91, H45, YN2 and P161 are deposited on an international basis as FERM BP-7373, FERM BP-7374, FERM BP-7375 and BP-7376, respectively, in National Institute of Advanced Industrial Science and Technology, International Patent Organism Depositary, under Budapest Treaty on international approval for deposition of microorganisms in terms of patent procedures.

For normal culture of microorganisms for use in production of PHA synthesizing enzymes according to the present invention, for example preparation of stock strains, and reproduction for securing the number of cells and their active states required for production of the PHA synthesizing enzyme, a culture medium containing components needed for growth of microorganisms to be used is appropriately selected and used. For example, any type of culture media such as general natural culture media (broths, yeast extracts, etc) and synthetic culture media with nutrient sources added thereto may be used unless they adversely affect growth and survival of microorganisms.

For the culture, any method such as liquid culture and solid culture may be used as long as reproduction of the microorganisms is possible. In addition, any type of culture including batch culture, fed batch culture, semi-continuous culture and continuous culture may be used. As for the form of the liquid batch culture, a method in which oxygen is supplied by shaking with a shaking flask, a method in which oxygen is supplied using a stirring aeration system with a jar fermenter and the like are employed. In addition, a multi-stage method in which these steps are connected in multiple stages may be employed.

In the case where the PHA synthesizing enzyme is produced using PHA producing microorganisms as described above, for example, a method in which the microorganism is grown in an inorganic culture medium containing alkanoic acid such as octanoic acid and nonanoic acid, and cells of the microorganism in the logarithmic growth phase to the early stage of the stationary phase are collected by centrifugation or the like to extract a desired enzyme, and so on may be used. Furthermore, if the microorganism is cultured using a condition as described above, mcl-PHA derived from added alkanoic acid is synthesized in a cell of the microorganism, but in this case, it is generally said that the PHA synthesizing enzyme exists in such a manner as to be bound to small particles of PHA produced in the cell. However, as a result of studies conducted by the inventors, it has been found that almost equivalent enzyme activity is present even in the supernatant liquid after conducting centrifugation of the liquid from fragmentation of cells cultured by any of the above described methods. It is assumed that this is because an almost equivalent amount of PHA synthesizing enzyme exists in a free state in a relatively early stage of culture, which is from the logarithmic growth phase to the early stage of the stationary phase as described above, since the enzyme is actively produced continuously in the cell.

For the inorganic culture medium for use in the above culture methods, any medium containing components enabling microorganisms to be grown such as phosphorous sources (e.g. phosphates) and nitrogen sources (e.g. ammonium salts, nitrates, etc.) may be used, and inorganic culture media may include, for example, a MSB medium, E medium (J. Biol. Chem., 218, 97–106 (1956)) and M9 medium. Furthermore, the composition of the M9 medium for use in Examples of the present invention is as follows:

$Na_2HPO_4$: 6.2 g
$KH_2PO_4$: 3.0 g
NaCl: 0.5 g
$NH_4Cl$: 1.0 g
(per liter of medium, pH 7.0).

In addition, about 0.3% (v/v) of a solution containing minor components shown below is preferably added in the above inorganic culture medium for ensuring satisfactory growth of the microorganism and production of the PHA synthesizing enzyme:

(Solution Containing Minor Components)
nitrilotriacetic acid: 1.5 g
$MgSO_4$: 3.0 g
$MnSO_4$: 0.5 g
NaCl: 1.0 g
$FeSO_4$: 0.1 g
$CaCl_2$: 0.1 g
$CoCl_2$: 0.1 g
$ZnSO_4$: 0.1 g
$CuSO_4$: 0.1 g
$AlK(SO_4)_2$: 0.1 g
$H_3BO_3$: 0.1 g
$Na_2MoO_4$: 0.1 g
$NiCl_2$: 0.1 g
(per liter)

The culture temperature may be any temperature at which the above microorganism can satisfactorily be grown, for example 14 to 40° C., preferably 20 to 35° C.

Also, a desired PHA synthesizing enzyme can be produced using a transformant having a PHA synthesizing enzyme gene of the aforesaid PHA producing microorganism. Cloning of the PHA synthesizing enzyme gene, preparation of an expression vector, and preparation of the transformant may be carried out in accordance with an established method. In a transformant obtained with a microorganism such as colibacillus as a host, the medium for use in culture is a natural medium or a synthetic medium, for example, a LB medium, M9 medium or the like. A culture temperature is in the range of from 25 to 37° C. In addition, aerobic culture is conducted for 8 to 27 hours to achieve growth of the microorganism. Thereafter, cells can be collected to collect the PHA synthesizing enzyme accumulated in the cells. Antibiotics such as kanamycin, ampicillin, tetracycline, chloramphenicol and streptomycin may be added in the medium as necessary. Also, in the case where an inductive promoter is used in the expression vector, an inductive material corresponding to the promoter may be added to the medium to promote expression when the transformant is cultured. Such inductive materials include, for example, isopropyl-1-thio-β-D-galactoside (IPTG), tetracycline and indolacrylic acid (IAA).

For the PHA synthesizing enzyme, liquids from fragmentation of cells of microorganism, and crude enzymes such as salted ammonium sulfate obtained by precipitation and collection of protein components with ammonium sulfate and the like may be used, or enzymes purified by various kinds of methods may be used. Stabilizers such as metal salts, glycerin, dithiothreitol, EDTA and bovine serum albumin (BSA), and activators may be added to the enzymes as necessary.

For isolation and purification of PHA synthesizing enzymes, any method allowing enzyme activation of PHA synthesizing enzymes to be retained may be used. For example, obtained cells of microorganism are crushed with a French press, a supersonic crusher, lysozyme, various kinds of surfactants and the like, and thereafter, for a crude enzyme solution obtained by centrifugation or salted ammonium sulfate prepared therefrom, means such as affinity chromatography, cation or anion exchange chromatography, and gel filtration is applied alone or in combination, whereby a purified enzyme can be obtained. In particular, a gene recombination protein can be purified more conveniently by expressing the protein in the form of united protein with "tags" such as histidine residues bound to the N terminal and C terminal, and making the protein to be bound to an affinity resin through these tags. For isolating a desired protein from the united protein, methods of cleaving the linkage by protease such as thrombin and a blood coagulation factor Xa, decrasing the pH, adding a high concentration of imidazole as a competitive binding agent and the like may be used. Alternatively, if the tag includes intein as in the case of using pTYB1 (manufactured by New EnglanBiolab Co., Ltd.) as a expression vector, a reduction condition is achieved by dithiothreitol or the like to cleave the linkage. For the united protein enabling purification by affinity chromatography, glutathione-S-transferase (GST), chitin bound domain (CBD), maltose bound protein (MBP) and thioredoxine (TRX) are also well known in addition to the histidine tag. The GST united protein can be purified by the GST affinity resin.

A various kinds of reported methods may be used for measuring activity of the PHA synthesizing enzyme, and for example, the activity may be measured by the following method in which as a measurement principle, CoA released in the process through which 3-hydroxyacyl CoA is polymerized under the catalytic action of the PHA synthesizing enzyme to form PHA is colored with 5,5'-dithiobis-(2-nitrobenzoic acid) to carry out measurements. Reagent 1: bovine serum albumin (manufactured by Sigma Co., Ltd.) is dissolved in a 0.1 M Tris hydrochloric buffer (pH 8.0) in the concentration of 3.0 mg/ml, Reagent 2: 3-hydroxyoctanoyl CoA is dissolved in a 0.1 M Tris hydrochloric buffer (pH 8.0) in the concentration of 3.0 mM, Reagent 3: trichloroacetic acid is dissolved in a 0.1 M Tris hydrochloric buffer (pH 8.0) in the concentration of 10 mg/ml, and Reagent 4: 5,5'-dithiobis-(2-nitrobenzoic acid) is dissolved in a 0.1 M Tris hydrochloric buffer (pH 8.0) in the concentration of 2.0 mM. First reaction (PHA synthesis reaction): 100 μl of Reagent 1 is added in 100 μl of sample (enzyme) solution and mixed together, and is pre-incubated at 30° C. for a minute. 100 μl of Reagent 2 is added thereto and mixed together, and is incubated at 30° C. for 1 to 30 minutes, followed by adding thereto Reagent 3 to stop the reaction. Second reaction (reaction of coloring free CoA): the first reaction solution of which reaction has been stopped is subjected to centrifugation (15,000×g, 10 minutes), and 500 μl of Reagent 4 is added in 500 μl of supernatant liquid of this solution, and is incubated at 30° C. for 10 minutes, followed by measuring an absorbance at 412 nm. Calculation of enzyme activity: the amount of enzyme for releasing 1 μmol of CoA per minute is defined as one unit (U).

<Process for Producing Electrophoretic Particles>

One example of process for production of electrophoretic particles containing micro-capsulated pigments of the present invention may be a process comprising at least steps of (1) dispersing pigments on an aqueous medium, (2) fixing a PHA synthesizing enzyme to the dispersed pigment, (3) adding 3-hydroxyacyl CoA as a substrate, (4) carrying out a PHA synthesis reaction and (5) collecting micro-capsulated pigment particles covered with PHA as electrophoretic particles, and processing the same as an electrophoretic particle dispersion system for use in an electrophoretic display device.

The step of dispersing the pigment on the aqueous medium is conducted by adding one or more selected pigments in the aqueous medium, and carrying out dispersion processing, followed by classifying the pigment in a desired range of particle size if necessary.

The pigment for use in the present invention may be an organic or inorganic pigment, but is preferably excellent in heat resistance and light resistance. Examples of organic pigments may include azo-based, phthalocyanine-based, benzimidasolone-based, quinacridone-based, isoindolynone-based, pyrathrone-based, dibromanzanthrone-based, indathrone-based, anthrapyrimidine-based, flavathrone-based, perylene-based, perynone-based, quinophtharone-based, phtharone-based, thioindigo-based, indigo-based, dioxazine-based, anthraquinone-based, xanthene-based, methine-based and azomethine-based pigments, and condensation polycyclic pigments including other metal complex pigments. Examples of inorganic pigments may include Milori blue, iron oxide, cobalt purple, manganese purple, ultramarine blue, Prussian blue, cobalt blue, celluriane blue, pyridiane, emerald green, cobalt green and red iron oxide, and one or two types thereof are appropriately selected and used. The above pigments may be used after being subjected to a various kinds of well known surface treatments. Examples of surface treatments include surfactant treatment, coupling treatment and pigment derivative treatment.

Dispersion processing may be carried out using a homo mixer, a horizontal mini mil, a ball mil, a roll mil, a sand grinder, a milling machine, a supersonic operation or the like. In addition, the dispersion may be carried out by a method in which mixtures are passed through a large number of nozzles under a hydraulic pressure of at least 1000 psi (about 70.3 $kg/cm^2$) in a liquid jet interaction chamber.

It is desirable that the pigment is dispersed in a single dispersion state in the range of from 0.05 μm to 4.5 μm for the particle size of the dispersed pigment. If the particle size of the dispersed pigment is not fallen in a desired range, classification by filtration and sedimentation processes can be carried out to make an adjustment.

The particle size of the dispersed pigment can be measured by known methods such as an absorbance method, a static light-scattering method, a dynamic light-scattering method and a centrifugal sedimentation method, and for example, an apparatus for measuring particle sizes such as Coulter counter multi-sizer may be used.

The composition of the aqueous medium for synthesis of PHA in this step may be any composition that allows the pigment to be dispersed in a desired state, and does not interfere the subsequent steps of fixing the enzyme to the pigment and carrying out the PHA synthesis reaction, but the composition may be adjusted into a composition allowing the activity of the PHA synthesizing enzyme to be exerted in order to simplify the subsequent steps. As the composition allowing the activity of the PHA enzyme to be exerted, for example, a buffer may be used. For the buffer, general buffers for use in biochemical reactions, for example, acetate buffers, phosphate buffers, potassium phosphate buffers, 3-(N-morpholino) propane sulfonate (MOPS) buffers, N-tris (hydroxymethyl) methyl-3-aminopropane sulfonate (TAPS) buffers, trischloride buffers, glycin buffers, and 2-(cyclohexylamino) ethanesulfonate (CHES) buffers are suitably used. The concentration of the buffer allowing the activity of the PHA synthesizing enzyme to be exerted may be a general concentration, namely in the range of from 5 mM to 1.0 M, but is preferably in the range of from 10 to 200 mM. Also, an adjustment is made so that pH is in the range of from 5.5 to 9.0, preferably from 7.0 to 8.5, but the possibility is not excluded that a pH condition is set in a range other than the above described range depending on the most suitable pH and pH stability of a PHA synthesizing enzyme to be used.

In addition, for maintaining a pigment dispersion condition in the aqueous medium, a suitable surfactant may be added as long as the surfactant has a type and concentration not interfering the subsequent steps, and has a type and concentration not interfering the purpose of the colored composition of the present invention. Examples of the surfactant may include, for example, anionic surfactants such as sodium oleate, sodium dodecylsulfonate, sodium dodecyl sulfate, sodium dodecyl-N-sarcosinate, sodium cholate, sodium deoxycholate and sodium taurodeoxycholate; cationic surfactants such as cetyltrimethylammonium bromide and dodecylpyridinium chloride; ampholytic surfactants such as 3-[(choleamidepropyl) dimethylammonio]-1-propanesulfonic acid (CHAPS), 3-[(3-choleamidepropyl) dimethylammonio]-2-hydroxy-1-propanesulfonic acid (CHAPSO), palmitoyllysolecithin and dodecyl-β-alanine; and nonionic surfactants such as octylglucoside, octylthioglucoside, heptylthioglucoside, decanoyl-N-methylglucamide (MEGA-10), polyoxyethylenedodecylether (Brij, Lubrol), polyoxyethylene-i-octylphenylether (Triton X), polyoxyethylenenonylphenylether (Nonidet P-40, Triton N), polyoxyethylene fatty acid ester (Span) and polyoxyethylenesorbitol ester (Tween).

In addition, for maintaining a pigment dispersion condition in the aqueous medium, a suitable auxiliary solvent may be added as long as the solvent has a type and concentration not interfering the subsequent steps, and has a type and concentration not interfering the purpose of the colored composition of the present invention. For the auxiliary solvent, one or two types of substances selected from, for example, linear aliphatic hydrocarbons such as hexane, and their derivatives such as monovalent alcohols such as methanol and ethanol, polyvalent alcohols such as glycerol, fatty acid ethers and carboxylates may be selected and used.

The step of fixing the PHA synthesizing enzyme to the pigment can be carried out by adding the PHA synthesizing enzyme in the aforesaid pigment dispersion, and subjecting the same to fixation processing. For the fixation processing, any method may be selected from enzyme fixation methods that are normally used as long as the method allows the activity of the enzyme to be retained, and are capable of being applied in desired pigments. For example, these methods may include a covalent binding method, ion absorption method, hydrophobic adsorption method, physical adsorption method, affinity adsorption method, crosslinking method and lattice inclusion method, but fixation methods using ion adsorption and hydrophobic adsorption are particularly convenient.

The enzyme protein such as a PHA synthesizing enzyme is a polypeptide in which a large number of amino acids are bound, and shows properties as an ion absorbent due to amino acids having free ionic groups such as lycine, histidine, arginine, asparaginic acid and glutamic acid, and have properties as a hydrophobic absorbent due to amino acids having free hydrophobic groups such as alanine, valine, leucine, isoleucine, methionine, tryptophane, phenylalanine and proline in terms that it is an organic macromolecule. Thus, the enzyme protein can be more or less adsorbed to a pigment having ionicity or hydrophobicity, or having both ionicity and hydrophobicity.

In the method in which the PHA synthesizing enzyme is fixed mainly by ion adsorption, a pigment expressing ionic functional groups on the surface may be used, and for example inorganic pigments having clay minerals, metal oxides and the like as main components may be used.

Also, in the method in which the PHA synthesizing enzyme is fixed mainly by hydrophobic adsorption, a pigment with having a nonpolar surface may be used, and for example azo pigments having a plurality of aromatic rings, organic pigments such as fused polycyclic phthalocyanine based pigments and anthraquinone based pigments, and inorganic pigments composed of carbon crystals such as carbon black may be used.

Fixation of the PHA synthesizing enzyme to the pigment by the ion adsorption or hydrophobic adsorption method is achieved by mixing the pigment and the PHA synthesizing enzyme together in a predetermined aqueous medium so that a predetermined concentration is obtained. At this time, it is desirable that the reaction vessel is shaken or stirred at a predetermined strength so that the enzyme can be evenly adsorbed to the surface of the pigment.

In the above described fixation processing, it is desirable that the composition of the aqueous medium in which the pigment and the enzyme are mixed together is determined in consideration of changes in positive and negative surface charge, the amount of charge and hydrophobicity of the pigment and PHA synthesizing enzyme due to the pH and salt concentration of the aqueous medium. For example, if the pigment is ion-adsorptive, the amount of charge contributing to adsorption between the pigment and the PHA synthesizing enzyme can be increased by reducing the salt concentration. Also, the opposite charge of the pigment and PHA synthesizing enzyme can be increased by changing pH. If the pigment is principally hydrophobic-adsorptive, hydrophobicities of the pigment and the PHA synthesizing enzyme can be increased by increasing the salt concentration. Also, the electrophoresis and wetting angle are measured in advance to examine charged conditions and hydrophobicity of the pigment and PHA synthesizing enzyme, whereby the composition suitable for adsorption can be determined. In addition, the amount of adsorption between the pigment and the PHA synthesizing enzyme can directly be measured to determine the composition. For measurements of the amount of adsorption, for example, a method may be used in which a solution of PHA synthesizing enzyme of which concentration is known is added in a solution with a pigment dispersed therein to carry out adsorption processing, followed by measuring the concentration of the PHA synthesizing enzyme in the solution and determining the amount of the adsorbed enzyme using a subtraction method.

In the case of a pigment to which the enzyme is hardly fixed by the ion adsorption method and hydrophobic adsorption method, the enzyme may be fixed to the pigment using the covalent binding method by conducting treatments allowing for possibilities of complication of operations and deactivation of the enzyme as necessary. For example, there are a method in which a pigment having aromatic amino groups is diazotized, and the enzyme is diazo-coupled thereto, a method in which a peptide linkage is formed between the pigment having a carboxyl group and amino group and the enzyme, a method in which alkylation is performed between the pigment having a halogen group and the amino group or the like of the enzyme, a method in which crosslinking is made between the amino group of the solid particle and the amino group of the enzyme, a method in which the pigment having a carboxyl group and amino group is reacted with the enzyme in the presence of a compound having an aldehyde group or a ketone group and an isocyanide compound, and a method in which an exchange reaction is carried out between the pigment having a disulfide group and the thiol group of the enzyme.

In addition, the enzyme may be fixed to a pigment with a ligand introduced therein by affinity adsorption. In this case, any substance may be selected as the ligand as long as it enables affinity adsorption while maintaining the activity of the PHA synthesizing enzyme. Also, the enzyme may be fixed by binding a different biopolymer such as a protein to the PHA synthesizing enzyme, and subjecting the bound biopolymer to affinity adsorption. The biopolymer may be bound to the PHA synthesizing enzyme by gene recombination or the like, or by a chemical process. For example, as described later in Examples, glutathione-S-transferase is united to the PHA synthesizing enzyme by transformation, and the united protein is adsorbed by affinity adsorption to sepharose having introduced therein glutathione as a ligand for glutathione-S-transferase, whereby the enzyme can be fixed.

Also, a peptide including amino acid sequences having binding capacity for the pigment can be united to the polyhydroxyalkanoate synthesizing enzyme and exhibited to fix the polyhydroxyalkanoate synthesizing enzyme on the surface of the pigment based on the bonding between the part of peptide corresponding to the amino acid sequence having binding capacity for the pigment and the pigment.

The amino acid sequence having binding capacity for the pigment can be determined by the screening of a random peptide library, for example. In particular, for example, a phage display peptide library prepared by coupling a random synthesis gene to the N-terminal gene of the surface protein of the M13 type phage (e.g. gene III protein) can be suitably used, but in this case, determination of the amino acid sequence having binding capacity for the pigment is carried out in accordance with the following procedure. Specifically, the phage display peptide library is added to the pigment to contact the phage to the pigment, followed by separating bound phages and non-bound phages by washing. The pigment-bound phage is eluted with an acid or the like and neutralized with a buffer solution, and colibacillus is thereafter infected with the phage to amplify the phage. If this screening process is repeated several times, a plurality of clones having binding capacity for a desired pigment are concentrated. Here, for obtaining a single clone, colonies are made on the culture plate with the phage with which colibacillus is infected again. Each single colony is cultured on the liquid culture medium, followed by precipitating and purifying the phage existing in the supernatant liquid of the medium by polyethylene glycol or the like, and analyzing the base sequence, whereby the structure of the peptide can be known.

The amino sequence of the peptide having binding capacity for the pigment, obtained by the above described method, is united to the polyhydroxyalkanoate synthesizing enzyme using a normal gene engineering methodology for use. The peptide having binding capacity for the pigment can be coupled to the N-terminal or C-terminal of the polyhydroxyalkanoate synthesizing enzyme to be expressed. The peptide can also be expressed with an appropriate spacer sequence inserted. The spacer sequence has preferably about 3 to 400 amino acids, and may include any amino acid. Most preferably, the spacer sequence neither prevents the PHA synthesizing enzyme from functioning nor prevents the PHA synthesizing enzyme from being bound to the pigment.

The pigment with the enzyme fixed thereto, prepared by the above described method, may be used directly, but may also be used after being subjected to freeze-drying or the like.

The amount of enzyme fixed to the pigment may be set in the range of from 10 units (U) to 1,000 units (U), desirably from 50 units (U) to 500 units (U) per 1 g of pigment, wherein one unit (U) is defined as the amount of PHA synthesizing enzyme when the amount of CoA released in the reaction through which PHA is synthesized by polymerization of 3-hydroxyacyl CoA equals 1 μmol per minute.

A time period over which fixation of the enzyme is carried out is desirably 1 minute to 24 hours, more desirably 10 minutes to 1 hour. Standing the sample at rest or leaving it to stand for excessively long time is not preferable because coagulation of pigments and reduction of enzyme activity may be caused.

Also, the enzyme may be fixed to the pigment by adding the pigment directly to the enzyme solution without carrying out the previous step of dispersing the pigment in the aqueous medium, and then dispersing the pigment in the enzyme solution. In this case, electric repulsion and steric hindrance associated with the ionic functional group possessed by the enzyme fixed to the pigment makes it possible to facilitate dispersion of the pigment in the aqueous medium and eliminate necessity to add a surfactant in the aqueous medium or reduce the amount of the surfactant.

The step of adding 3-hydroxyacyl CoA as a substrate is achieved by adding a preserved solution of 3-hydroxyacyl CoA separately prepared to the aqueous dispersion of the pigment with the enzyme fixed thereto in the previous step so that a desired concentration is reached. 3-hydroxyacyl CoA as a substrate is added in final concentrations of generally from 0.1 mM to 1.0 M, desirably from 0.2 mM to 0.2 M, and further preferably 0.2 mM to 1.0 mM.

Also, in the above describe step, the composition such as type and concentration of 3-hydroxyacyl CoA in the aqueous reaction solution is changed with time, thereby making it possible to change the composition of the monomer unit of PHA covering the pigment in the direction extending from the inside toward the outside of the pigment.

The form of this pigment with the monomer unit composition changed may be, for example, a form in which the change of the composition of the PHA cover is continuous, and the pigment is covered with one layer of PHA having a gradient of composition formed in the direction extending from the inside toward the outside. The production method may be, for example, a method in which 3-hydroxyacyl CoA of different composition is added in the reaction solution while synthesizing PHA.

In addition, as another form, there may be a form in which the composition of the PHA cover is changed by stages, and PHA of different compositions covers the pigment in multiple layers. The production method for this form may be a method in which PHA is synthesized with a certain composition of 3-hydroxyacyl CoA, followed by collecting the pigment under preparation from the reaction solution on a temporary basis using centrifugation or the like, and adding thereto a reaction solution of 3-hydroxyacyl CoA of different composition again, and so on.

The step of carrying out a PHA synthesis reaction is carried out by preparing the composition of reaction solution so that a composition allowing activity of the PHA synthesizing enzyme to be exerted can be obtained if the composition of reaction solution has not been prepared till the previous step, and adjusting the reaction temperature and reaction time, in order that a micro-capsulated pigment having a desired shape can be obtained by PHA to be synthesized.

The concentration of the buffer for the reaction solution allowing the activity of the PHA synthesizing enzyme to be exerted may be a general concentration, namely a concentration in the range of from 5 mM to 1.0 M, but is desirably a concentration in the range of from 10 to 200 mM. For pH, an adjustment is made so that the pH is in the range of from 5.5 to 9.0, preferably from 7.0 to 8.5, but the possibility is not excluded that a pH condition is set in a range other than the above described range depending on the most suitable pH and pH stability of a PHA synthesizing enzyme to be used.

The reaction temperature is set as appropriate depending on the property of the PHA synthesizing enzyme to be used, but may be set normally at 4 to 50° C., preferably at 20 to 40° C. However, the possibility is not excluded that a temperature condition is set in a range other than the above described range depending on the most suitable temperature and heat resistance of a PHA synthesizing enzyme to be used.

The reaction time is appropriately selected and set within the range of normally from 1 minute to 24 hours, preferably from 30 minutes to 3 hours depending on stability, etc. of the PHA synthesizing enzyme to be used.

The micro-capsulated pigment is obtained by this step, but the structure of monomer units of PHA constituting the microcapsule can be determined by extracting PHA from the micro-capsulated pigment with chloroform, and thereafter carrying out composition analysis by gas chromatography or the like, or using a time-of-flight secondary ion mass spectrometer (TOF-SIMS) and an ion sputtering technique.

The molecular weight of PHA is not particularly limited, but the number-average molecular weight is desirably in the range of from 1,000 to 10,000,000, more preferably from 3,000 to 1,000,000 for maintaining strength of the micro-capsulated pigment, and providing a stable amount of charge. The molecular weight of PHA may be measured by GPC (gel permeation chromatography) after PHA is extracted from the micro-capsulated pigment with chloroform.

Also, in the method of producing the micro-capsulated pigment according to the present invention, density of the pigment in the microcapsule can be increased because the pigment can be directly covered with PHA. On the other hand, however, it is required that the amount of PHA covering the pigment should be increased to enhance dispersibility and mechanical strength of the micro-capsulated pigment, and consequently, the amount of PHA covering the pigment is, for example, in the range of from 1 to 30% by mass, preferably from 1 to 20% by mass, more preferably 1 to 15% by mass of the weight of the pigment.

The particle size of the micro-capsulated pigment obtained by the above step is 50 μm or smaller, preferably 10 μm or smaller, more preferably 0.01 to 10 μm. The particle size of the micro-capsulated pigment can be measured by known methods such as an absorbance method, a static light-scattering method, a dynamic light-scattering method and a centrifugal sedimentation method, and for example, an apparatus for measuring particle sizes such as a Coulter counter multi-sizer may be used.

In addition, the micro-capsulated pigment obtained by this step may be subjected to various kinds of secondary treatments and processing such as chemical modification before being used.

For example, a micro-capsulated pigment having further useful functions and properties can be obtained by subjecting PHA on the surface of the pigment to chemical modification. For example, a graft chain is introduced, whereby a micro-capsulated pigment having various kinds of properties derived from the graft chain can be obtained. If polysiloxane as described later is introduced as a graft chain, for example, a micro-capsulated pigment having improved mechanical strength, dispersibility, weather resistance, water repellency (resistance), heat resistance and the like can be obtained, and storage stability and weather resistance of electrophoretic particles using the pigment can be improved. In addition, if the micro-capsulated pigment is used in an electrophoretic display device with dyes contained in an insulating medium, it can be expected that contamination of electrophoretic particles with dyes is curbed. In addition, by having PHA on the surface of the pigment crosslinked, mechanical strength, chemical resistance, heat resistance and the like of the micro-capsulated pigment can be improved.

The method for chemical modification is not particularly limited as long as it is a method by which the purpose of obtaining a desired function and structure is achieved, but, for example, a method in which PHA having a reactive functional group on the side chain is synthesized, and chemical modification is accomplished using the chemical reaction of the functional group may be used as a suitable method.

The type of the above described reactive functional group is not particularly limited as long as it serves the purpose of obtaining a desired function and structure, and may be, for example, an epoxy group as described previously. PHA having an epoxy group on the side chain can be chemically converted as in the case of a normal polymer having an epoxy group. Specifically, for example, conversion into a hydroxyl group, and introduction of a sulfone group are possible. Also, a compound having thiol and amine can be added, and for example, a compound having a reactive functional group at the terminal, specifically a compound having an amino group having high reactivity with the epoxy group is added and reacted, whereby the graft chain of polymer is formed.

Compounds having amino groups on the terminals may include, for example, polyvinyl amine, polyethylene imine, and amino modified polymers such as amino modified polysiloxane (amino modified silicone oil). Among them, for amino modified polysiloxane, commercially available modified silicone oil, or amino modified polysiloxane that is synthesized by a method described in J.Amer. Chem. Soc., 78, 2278 (1956) or the like may be used, and the effect of improving mechanical strength, dispersibility, light resistance, weather resistance, water repellency (resistance) and heat resistance and so on by addition of the graft chain of the polymer can be expected.

In addition, another example of chemical conversion of a polymer having an epoxy group is a crosslinking reaction by a diamine compound such as hexamethylenediamine, succinic anhydrate, 2-ethyl-4-methylimidazole, or the like, and an example of physicochemical conversion is a crosslinking reaction by irradiation with electron rays or the like. Among them, the reaction between PHA having an epoxy group on the side chain and hexamethylenediamine progresses in accordance with a scheme as described below to produce a crosslinked polymer.

[70]

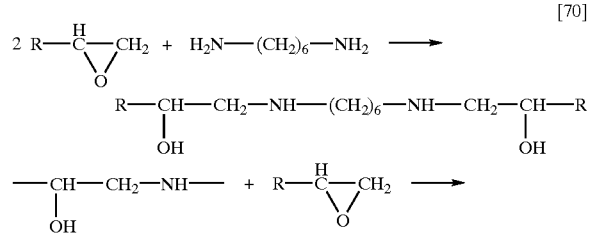

-continued

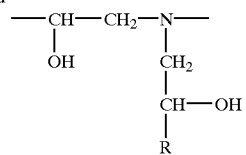

In the step of collecting the micro-capsulated pigment covered with PHA as electrophoretic particles, and processing the collected particles as an electrophoretic particle dispersion system for use in an electrophoretic display device, the particles of micro-capsulated pigment covered with PHA in the aqueous system are substituted for the insulating medium that is actually used in the electrophoretic display device. In this step, the reaction solution after the enzyme reaction is processed by a well known method such as filtration under reduced pressure, filtration under pressure or centrifugation to obtain a water bearing cake of electrophoretic particles. This water bearing cake is resuspended in the insulating medium after being dried or without being dried, and washing by the insulating medium is repeated, thereby replacing the insulating medium. For the medium in which electrophoretic particles are dispersed, a medium having low solvency for electrophoretic particles and thus being capable of dispersing electrophoretic particles with stability, and having insulating properties such that no ions are contained and no ions are produced by application of voltage is used. A medium having a specific gravity almost equal to that of electrophoretic particles to prevent sink-and-float of electrophoretic particles, and having a low viscosity in terms of mobility of electrophoretic particles at the time of application of voltage is used. For example, hexane, decane, hexadecane, kerosene, toluene, xylene, olive oil, tricresyl phosphate, isopropanol, trichlorotrifluoroethane, dibromotetrafluoroethane and tetrachloroethylene may be used, and mixtures thereof may be used to match the specific gravity with that of electrophoretic particles for preventing sink-and-float of electrophoretic particles.

The electrophoretic display device using electrophoretic particles of the present invention is constructed by enclosing an insulating medium dispersion liquid for the electrophoretic particles of the present invention in a space formed by placing a pair of electrode plates in a opposite manner at a predetermined interval, and providing control means for applying a controlling voltage to between the above described electrode plates to change the state of distribution of electrophoretic particles in the above described dispersion system. As one example, a sectional view of the electrophoretic display device having such an aspect is shown in FIGS. 1A and 1B. The electrophoretic display device of FIGS. 1A and 1B comprises a first electrode, a second electrode to which a voltage different from that of the first electrode is applied, a plurality of electrophoretic particles moving between the first and second electrodes, a first substrate, a second substrate placed opposite to the first substrate, and a transparent insulating liquid 3 filling between the first and second substrates and holding the plurality of electrophoretic particles, wherein the first electrode is placed in the central part of the first substrate, the second electrode is placed at the end of the first substrate, and the internal surface of the second substrate is shaped so that light is focused in the central part of the first substrate.

Whether the electrophoretic particles are charged positively or negatively in the insulating liquid depends on the type of polyhydroxyalkanoate and the type of insulating liquid, but either a positive or negative charge is acceptable in the present invention.

If the electrophoretic particles are positively charged in the insulating liquid, the electrophoretic particles are electrophoresed and deposited on the negative second electrode 6 when the power circuit is connected as shown in FIG. 1A. Even when the electric connection between the power circuit and the first electrode 5 and second electrode 6 is disconnected in this state, the positively charged electrophoretic particles 4 retains a state in which they are attracted onto the second electrode 6 due to electrostatic attraction by a electrostatic capacity generated in the area in which the first electrode 5 is superimposed on the second electrode 6. Also, in the case where the positively charged electrophoretic particles 4 are deposited on the negative first electrode 5 (FIG. 1B), even when the electric connection between the power circuit and the first electrode 5 and second electrode 6 is disconnected, repulsion by electrostatic force (repulsive force) by the electrostatic capacity generated in the area in which the first electrode 5 is superimposed on the second electrode 6 makes the positively charged electrophoretic particles 4 retain the state in which they remain on the first electrode 5. Accordingly, a memory holding power for the electrophoretic particles 4 to be deposited on the electrode can sufficiently be maintained, and power consumption can be reduced.

The electrophoretic particles 4 in the insulating liquid 3 can be moved on both the electrodes by changing the polarity of voltages applied to the first electrode 5 and second electrode 6.

For example, if the first electrode 5 is a positive electrode, and the second electrode 6 is a negative electrode for the positively charged electrophoretic particles 4, the electrophoretic particles 4 are attracted onto the second electrode 6 by electrostatic attraction, and the electrophoretic particles 4 are collected on the second electrode 6 located in the periphery of the bottom of the concave space (FIG. 1A).

Conversely, if the first electrode 5 is a negative electrode, and the second electrode 6 is a positive electrode, the electrophoretic particles 4 are attracted onto the first electrode 5 by electrostatic attraction, and the electrophoretic particles 4 are collected on the first electrode 5 located in the central part of the bottom of the concave space (FIG. 1B). Display can be provided by using this phenomenon.

For example, if the electrophoretic particles 4 are collected on the first electrode 5 in the central part, the color of the electrophoretic particles 4 is observed from the observation side (second substrate 2) due to the light collecting effect associated with the concave shape.

Conversely, if the electrophoretic particles 4 are collected on the second electrode 6 located in the periphery of the bottom of the concave space, the colors of colored layers having optical properties (hue, reflectivity, etc.) different from those of the electrophoretic particles 4, such as an insulating layer 7, the first electrode 5, the first substrate 1 or a colored layer placed on the first substrate 1 can be observed from the observation side (second substrate 2) due to the light collecting effect associated with the concave shape. When the colored layer is formed, the colored layer may be formed in a pattern or over the entire surface. In addition, a light reflecting layer may be provided below the colored layer.

For example, if the positively charged electrophoretic particles 4 are black and the first electrode 5 is white, black-and-white display can be provided, wherein the second substrate 2 and the insulating layer 7 should be transparent.

If the electrophoretic particles 4 are colored (e.g. yellow, cyan, magenta, etc.), color display can be provided.

The present invention will be more specifically described below using Examples. However, each of the Examples that will be described below represents one example of the most preferred embodiments of the present invention, but the technical scope of the present invention should not be limited to these Examples.

REFERENCE EXAMPLE 1

Preparation of Transformant Capable of Producing PHA Synthesizing Enzyme, and Production of PHA Synthesizing Enzyme A transformant capable of producing the PHA synthesizing enzyme was prepared by the following method.

The YN2 strain was cultured on 100 ml of LB culture medium (1% polypeptone, 0.5% yeast extract, 0.5% sodium chloride, pH 7.4) at 30° C. overnight, followed by isolating and collecting chromosome DNA using a method by Marmer, et al. The obtained chromosome DNA was fully decomposed with a restriction enzyme Hind III. pUC18 was as a vector and cleaved by the restriction enzyme Hind III. Dephosphorylation of the terminal (Molecular Cloning, 1, 572, (1989); Cold Spring Harbor Laboratory Press.) was carried out, and thereafter DNA Ligation Kit Ver. 11 (Takara Shuzo Co., Ltd.) was used to couple the cleaved site (cloning site) of the vector to the Hind III fully decomposed fragment of the chromosome DNA. A plasmid vector with this chromosome DNA fragment incorporated therein was used to transform the *Escherichia coli* HB101 strain to prepare a DNA library of the YN2 strain.

Then, for selecting the DNA fragment including the PHA synthesizing enzyme gene of the YN2 strain, a probe for colony hybridization was prepared. Oligonucleotides composed of base sequences of SEQ ID NO: 5 and SEQ ID NO: 6 were synthesized (Amasham Pharmacia.Biotech), and these oligonucleotides were used as primers to carry out PCR with the chromosome DNA as a template. The PCR-amplified DNA fragment was used as a probe. The labeling of the probe was carried out using the commercially available labeling enzyme AlkPhosDirect (Amasham Pharmacia.Biotech). The obtained labeled probe was used to select *Escherichia coli* strains having recombinant plasmids including PHA synthesizing enzyme genes from the chromosome DNA library of YN2 strains by the colony hybridization method. Plasmids were collected from the selected strains by the alkali method, whereby the DNA fragment including the PHA synthesizing enzyme gene can be obtained.

The gene DNA fragment obtained here was recombined into a vector pBBR 122 (Mo Bi Tec) including a broad-host-range replication region belonging to none of Inc P, Inc Q and Inc W constituting an incompatibility group. When this recombinant plasmid was transformed into the *Pseudomonas cichorii* YN2 ml strain (strain lacking PHA synthesis capability) by the Electroporation method, PHA synthesizing capability of the YN2 ml strain was recovered, thus exhibiting complement property. Thus, it is ensured that the selected gene DNA fragment includes a PHA synthesizing enzyme gene domain capable of being translated into the PHA synthesizing enzyme in *Pseudomonas cichorii* YN2 ml strain.

For this DNA fragment including the PHA synthesizing enzyme gene, base sequences were determined by the Sanger's method. As a result, it was found that in the determined base sequences, there existed base sequences expressed by SEQ ID NO: 2 and SEQ ID NO: 4, each coding a peptide. As described below, it could be ensured that the proteins composed of individual peptide chains all had enzyme activity, and the base sequences expressed by SEQ ID NO: 2 and SEQ ID NO: 4 were PHA synthesizing enzymes. Specifically, it was ensured that the base sequence of SEQ ID NO: 2 coded the amino acid sequence expressed by SEQ ID NO: 1, and the base sequence of SEQ ID NO: 4 coded the amino acid sequence expressed by SEQ ID NO: 3, and the PHA synthesis capability can be exhibited with a protein having only any one of these amino acid sequences.

For the PHA synthesizing enzyme gene of base sequence expressed by SEQ ID NO: 2, PCR was carried out with Chromosome DNA as a template to reprepare the full length of the PHA synthesizing enzyme.

For the base sequence expressed by SEQ ID NO: 2, oligonucleotide having base sequences upstream to its initiation codon (SEQ ID NO: 7), which serves as an upstream primer, and oligonucleotide having base sequences downstream to its stop codon (SEQ ID NO: 8), which serves as a downstream primer were designed and synthesized, respectively (Amasham Pharmacia.Biotech) Using these oligonucleotides as primers, PCR was carried out with chromosome DNA as a template to amplify the full length of the PHA synthesizing enzyme gene (LA-PCR Kit; Takara Shuzo Co., Ltd.).

In a similar way, for the PHA synthesizing enzyme gene of base sequence expressed by SEQ ID NO: 4, PCR was carried out with Chromosome DNA as a template to reprepare the full length enzyme of the PHA synthesizing enzyme. For the base sequence expressed by SEQ ID NO: 4, oligonucleotide having base sequences upstream to its initiation codon (SEQ ID NO: 9), which serves as an upstream primer, and oligonucleotide having base sequences downstream to its stop codon (SEQ ID NO: 10), which serves as a downstream primer were designed and synthesized, respectively (Amasham Pharmacia.Biotech). Using this oligonucleotide as a primer, PCR was carried out to amplify the full length gene of the PHA synthesizing enzyme (LA-PCR Kit; Takara Shuzo Co., Ltd.).

Then, PCR amplified fragment including the obtained full length gene of PHA synthesizing enzyme were each fully decomposed using the restriction enzyme Hind III. In addition, the expression vector pTrc99A was also cleaved with the restriction enzyme Hind III, and was subjected to dephosphorylation processing (Molecular Cloning, vol. 1, p. 572, 1989; Cold Spring Harbor Laboratory Press). A DNA fragment including the full length gene of the PHA synthesizing enzyme gene with unnecessary base sequences at both terminals removed was coupled to the cleaved site of this expression vector pTrc99A using DNA Ligation Kit Ver. II (Takara Shuzo Co., Ltd.).

*Escherichia coli* (HB101: Takara Shuzo Co., Ltd.) was transformed by a potassium chloride method using the obtained recombinant plasmid. The obtained recombinant was cultured, amplification of recombinant plasmid was carried out, and the recombinant plasmid was collected for each type. The recombinant plasmid retaining gene DNA of SEQ ID NO: 2 was defined as pYN2-C1 (derived from SEQ ID NO: 2), and the recombinant plasmid retaining gene DNA of SEQ ID NO: 4 was defined as pYN2-C2 (derived from SEQ ID NO: 4).

*Escherichia coli* (strain HB101fB, fadB deficient mutant) was transformed by a potassium chloride method using pYN2-C1 and pYN2-C2 to obtain recombinant *Escherichia coil* strains, a pYN2-C1 recombinant strain and a pYN2-C2 recombinant strain each having its own recombinant plasmid.

The pYN2-C1 recombinant strain and pYN2-C2 recombinant strain were each plated in 200 ml of M9 medium containing 0.5% of yeast extract and 0.1% of octanoic acid, and were subjected to shaking culture at 37° C. and 125 strokes/minute. After 24 hours, cells were collected by centrifugation, and plasmid DNA was collected using an ordinary method.

For pYN2-C1, oligonucleotide serving as an upstream primer (SEQ ID NO: 11) and oligonucleotide serving as a downstream primer (SEQ ID NO: 12) were each designed and synthesized (Amasham Pharmacia.Biotech). Using these oligonucleotides as primers, PCR was carried out with pYN2-C1 as a template to amplify the full length gene of the PHA synthesizing enzyme having the BamHI restriction site in the upstream and the XhoI restriction site in the downstream (LA-PCR Kit; Takara Shuzo Co., Ltd.).

In a similar way, for pYN2-C2, oligonucleotide serving as an upstream primer (SEQ ID NO: 13) and oligonucleotide serving as a downstream primer (SEQ ID NO: 14) were each designed and synthesized (Amasham Pharmacia.Biotech). Using this oligonucleotide as a primer, PCR was carried out with pYN2-C2 as a template to amplify the full length gene of the PHA synthesizing enzyme having the BamHI restriction site in the upstream and the XhoI restriction site in the downstream (LA-PCR Kit; Takara Shuzo Co., Ltd.).

Each of purified PCR amplified products was digested by BamHI and XhoI, and was inserted into a corresponding site of plasmid pGEX-6P-1 (manufactured by Amasham Pharmacia.Biotech Co., Ltd.). These vectors were used to transform *Escherichia coli* (JM109) to obtain a strain for expression. The strain was checked with DNA fragments obtained by treating with BamHI and XhoI plasmid DNA prepared in large quantity using Miniprep (Wizard Minipreps DNA Purification Systems, manufactured by PROMEGA Co., Ltd.). The obtained strain was pre-cultured in 10 mL of LB-Amp medium overnight, and thereafter 0.1 mL of the strain was added in 10 mL of LB-Amp medium, and was shaking-cultured at 170 rpm at 37° C. for 3 hours. Thereafter, IPTG was added (at a final concentration of 1 mM), and culture was continuously carried out at 37° C. for 4 to 12 hours.

IPTG-induced *Escherichia coli* was collected (8000×g, 2 minutes, 4° C.), and was resuspended in 1 ml of PBS at 4° C. The cells were crushed by freezing and thawing and sonication, and were subjected to centrifugation (8000×g, 10 minutes, 4° C.) to remove solid contaminants. The presence of desired expression proteins in the supernatant was confirmed with SDS-PAGE, followed by purifying the induced and expressed GST fused protein with Glutathion Sepharose 4B beads (manufactured by Amasham Pharmacia.Biotech Co., Ltd.).

The glutathion sepharose for use in the purification was treated for curbing nonspecific adsorption in advance. Specifically, the glutathion sepharose was washed three times with the same amount of PBS (8000×g, 1 minute, 4° C.), and thereafter the same amount of PBS containing 4% BSA was added to treat the glutathion sepharose at 4° C. for 1 hour. After treatment, the glutathion sepharose was washed two times with the same amount of PBS, and was resuspended in ½ in quantity of PBS. 40 µL of pretreated glutathion sepharose was added to 1 mL of cell-free extract and stirred gently at 4° C. Thereby, the fused proteins GST-YN2-C1 and GST-YN2-C2 were adsorbed to glutathion sepharose.

After they were adsorbed, glutathion sepharose was collected by centrifugation (8000×g, 1 minute, 4° C.), and was washed three times with 400 μL of PBS. Thereafter, 40 μL of 10 mM of glutathion was added, and was stirred at 4° C. for 1 hour to elute the adsorbed fused protein. The supernatant was collected after centrifugation (8000×g, 2 minutes, 4° C.), and thereafter dialysis was conducted against PBS to purify the GST fused protein. It was confirmed by SDS-PAGE that the protein exhibited a single band.

500 μg of each GST fused protein was digested by PreScission protease (Amasham Pharmacia.Biotech, 5U), and was thereafter passed through glutathion sepharose to remove the protease and GST. Flow-through fractions were further processed with a sephadex G200 column equilibrated with PBS to obtain final purified expression proteins YN2-C1 and Yn2-C2. It was confirmed by SDS-PAGE that they exhibited single bands of 60.8 kDa and 61.5 kDa, respectively.

Each crude enzyme solution was concentrated using a biological solution sample concentrating agent (Mizubutorikun AB-1100, manufactured by Ato Co., Ltd.) to obtain 10 U/ml of purified enzyme solution.

The activity of each purified enzyme was measured by the aforesaid method. Also, the concentrations of proteins in the sample were measured by the Micro BCA protein quantification reagent kit (Pierce Chemical Co., Ltd.). The result of measuring the activity of each purified enzyme is shown in Table 1.

TABLE 1

|        | Activity | Specific Activity |
|--------|----------|-------------------|
| YN2-C1 | 2.1 U/mL | 4.1 U/mg Protein  |
| YN2-C2 | 1.5 U/mL | 3.6 U/mg Protein  |

REFERENCE EXAMPLE 2

Production of PHA Synthesizing Enzyme 2

P91, H45, YN2 or P161 strain was plated in the 200 ml of M9 medium containing 0.5% of yeast extract (manufactured by Difco Co., Ltd.) and 0.1% of octanoic acid, and was subjected to shaking culture at 30° C. and 125 strokes/minute. After 24 hours, cells were collected by centrifugation (10,000×g, 4° C., 10 minutes), and were resuspended in 200 ml of 0.1 M Tris HCl buffer (pH 8.0) and subjected to centrifugation again, thereby washing the cells. The cells were resuspended in 2.0 ml of 0.1 M Tris HCl buffer (pH 8.0) and crushed by a supersonic crusher, followed by centrifugation (12,000×g, 4° C., 10 minutes) and collection of a supernatant to obtain a crude enzyme. The result of measuring activity of each crude enzyme is shown in Table 2.

TABLE 2

|             | Activity |
|-------------|----------|
| P91 strain  | 0.1 U/mL |
| H45 strain  | 0.2 U/mL |
| YN2 strain  | 0.4 U/mL |
| P161 strain | 0.2 U/mL |

Each crude enzyme solution was concentrated using a biological solution sample concentrating agent (Mizubutorikun AB-1100, manufactured by Ato Co., Ltd,) to obtain 10 U/ml of purified enzyme solution.

REFERENCE EXAMPLE 3

Synthesis of 3-hydroxyacyl CoA (R)-3-hydroxyoctanoyl-CoA was synthesized in accordance with the following procedure, based on the method of Rehm BHA, Kruger N, Steinbuchel A (1998) Journal of Biological Chemistry 273 pp 24044–24051, with the method slightly modified. Acyl-CoA synthetase (manufactured by Sigma Co., Ltd.) was dissolved in a tris hydrochloric buffer solution (50 mM, pH 7.5) containing 2 mM ATP, 5 mM $MgCl_2$, 2 mM coenzyme A and 2 mM (R)-3-hydroxyoctanoate so that the concentration was 0.1 milliunit per microliter. The solution was stored in a hot bat at 37° C., and was sampled at appropriate times to analyze the progress of the reaction by HPLC. Sulfuric acid was added in the sampled reaction solution to make a concentration 0.02 N to stop the enzyme reaction, and thereafter (R)-3-hydroxyoctanoate being an unreacted substrate was extracted with n-heptane and removed. For the analysis by HPLC, using a RP18 column (nucleosil C18, 7 μm, Knauser), elution was conducted with the linear concentration gradient of acetonitrile using a 25 mM phosphate buffer solution (pH 5.3) as a mobile phase, and absorption spectra of 200 to 500 nm were monitored by a diode array detector, thereby detecting a thioester compound produced through the enzyme reaction. In a similar way, (R)-3-hydroxy-5-phenylvaleryl CoA, (R)-3-hydroxy-5-(4-fluorophenyl) valeryl CoA, (R,S)-3-hydroxy-5-phenoxyvaleryl CoA and (R,S)-3-hydroxy-7,8-epoxyoctanoyl CoA were prepared. Furthermore, (R,S)-3-hydroxy-7,8-epoxyoctanoic acid for use in preparation of (R,S)-3-hydroxy-7,8-epoxyoctanoyl CoA was prepared by epoxidizing unsaturated parts of 3-hydroxy-7-octenoic acid synthesized by the method described in Int. J. Biol. Macromol., 12, 85–91 (1990) with 3-chlorobenzoic acid.

EXAMPLE 1

Preparation of Electrophoretic Particles 1

Carbon black was suspended in the concentration of 25% by mass as a pigment in a 20 mM phosphate buffer solution (pH 7.0) with 1% by mass of Tween-20 added therein as a surfactant. They were mixed by a ball mill to prepare a dispersion of carbon black. According to the laser light scattering method, the carbon black was monodispersed with the average particle size of 1.2 μm.

The PHA synthesizing enzyme YN2-C1 derived from *Pseudomonas cichorii* YN2 prepared in Reference Example 1 was added to make a concentration 100 U/mL, and was left to stand at 20° C. for 30 minutes. Then, (R)-3-hydroxyoctanoyl CoA prepared in Reference Example 3 was added at a final concentration of 5 mM. A synthesis reaction was carried out by incubating the resulting solution at 37° C. for 30 minutes.

The reaction solution was subjected to centrifugation (10,000×g, 4° C., 10 minutes) to obtain a water-bearing cake of electrophoretic particles with carbon black as a core. This water-bearing cake was resuspended in ethanol, followed by collecting electrophoretic particles again by centrifugation operation. This operation was repeated three times to carry out dehydration processing. Then, the electrophoretic particles were suspended with kerosene, and centrifugation and washing were repeatedly carried out, thereby substituting the dispersion medium for kerosene.

When the prepared electrophoretic particles were dyed with Nile blue A, a reagent having a property of binding specifically to PHA to emit fluorescence, and was then observed by a fluorescence microscope (330 to 380 nm excitation filter, 420 nm long path absorption filter, manufactured by Nikon Co., Ltd.), fluorescence existed on the surface of the carbon black particle, and therefore the electrophoretic particle was found to be a capsule structure with carbon black as a core and PHA as a shell.

Figure 3A:
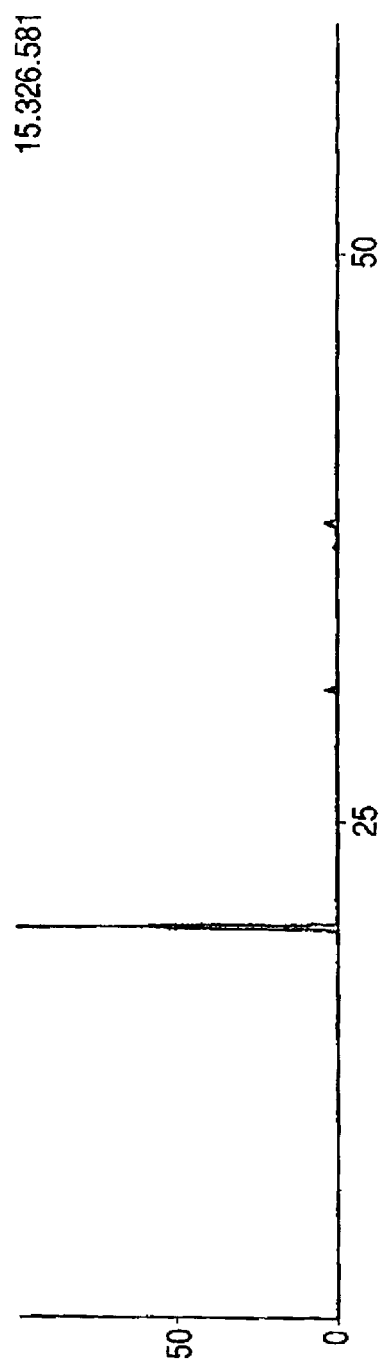
FIGS. 3A and 3B show results of GC-MS analysis of the outer shell of electrophoretic particles of Example 1.
Figure 3B:
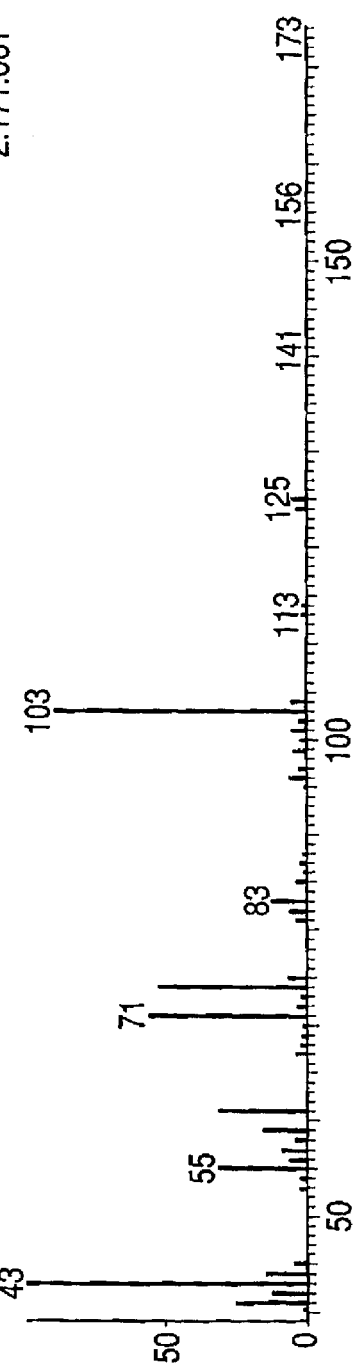

In addition, the electrophoretic particles were dried under reduced pressure, and were thereafter suspended in 20 ml of chloroform and stirred at 60° C. for 20 hours to extract PHA constituting shells. The extract was filtered by a membrane filter having a pore size of 0.45 μm, and was concentrated under reduced pressure by a rotary evaporator, followed by carrying out methanolysis in accordance with an ordinary method and conducting analyses by a gas chromatography-mass spectrometer (GC-MS, Shimadzu QP-5050, E1 method) to identify methyl-esterified PHA monomer units. As a result, the PHA was found to be PHA having 3-hydroxyoctanoic acid as a monomer unit as shown in FIGS. 3A and 3B. In addition, the molecular weight of the PHA was examined by gel permeation chromatography (GPC; Toso HLC-8020, column; Polymer laboratory PL gel MIXED-C (5 μm), solvent; chloroform, column temperature; 40° C., polystyrene equivalent) to obtain the result of Mn=21,000 and Mw=40,000.

According to the laser light scattering method, the electrophoretic particles were monodispersed with the average particle size of 1.8 μm.

EXAMPLE 2

Preparation of Electrophoretic Particles 2

A phthalocyanine based organic pigment, Pigment Blue 60 was suspended in the concentration of 25% by mass as a pigment in a 20 mM phosphate buffer solution (pH 7.0) with 1% by mass of Tween-20 added therein as a surfactant. They were mixed by a ball mill to prepare a dispersion of Pigment Blue 60. According to the laser light scattering method, the Pigment Blue 60 was monodispersed with the average particle size of 1.1 μm.

The PHA synthesizing enzyme YN2-C2 derived from Pseudomonas cichorii YN2 prepared in Reference Example 1 was added to make a concentration was 100 U/mL, and was left to stand at 20° C. for 30 minutes. Then, (R)-3-hydroxy-5-phenylvaleryl CoA prepared in Reference Example 3 was added at a final concentration of 5 mM. A synthesis reaction was carried out by incubating the resulting solution at 37° C. for 30 minutes.

The reaction solution was subjected to centrifugation (10,000×g, 4° C., 10 minutes) to obtain a water-bearing cake of electrophoretic particles with Pigment Blue 60 as a core. This water-bearing cake was resuspended in ethanol, followed by collecting electrophoretic particles again by centrifugation operation. This operation was repeated three times to carry out dehydration processing. Then, the electrophoretic particles were suspended with kerosene, and centrifugation and washing were repeatedly carried out, thereby substituting the dispersion medium for kerosene.

When the prepared electrophoretic particles were dyed with Nile blue A, a reagent having a property of binding specifically to PHA to emit fluorescence, and was then observed by a fluorescence microscope (330 to 380 nm excitation filter, 420 nm long path absorption filter, manufactured by Nikon Co., Ltd.), fluorescence existed on the surface of the Pigment Blue 60 particle, and therefore the electrophoretic particle was found to be a capsule structure with Pigment Blue 60 as a core and PHA as a shell.

Figure 4A:
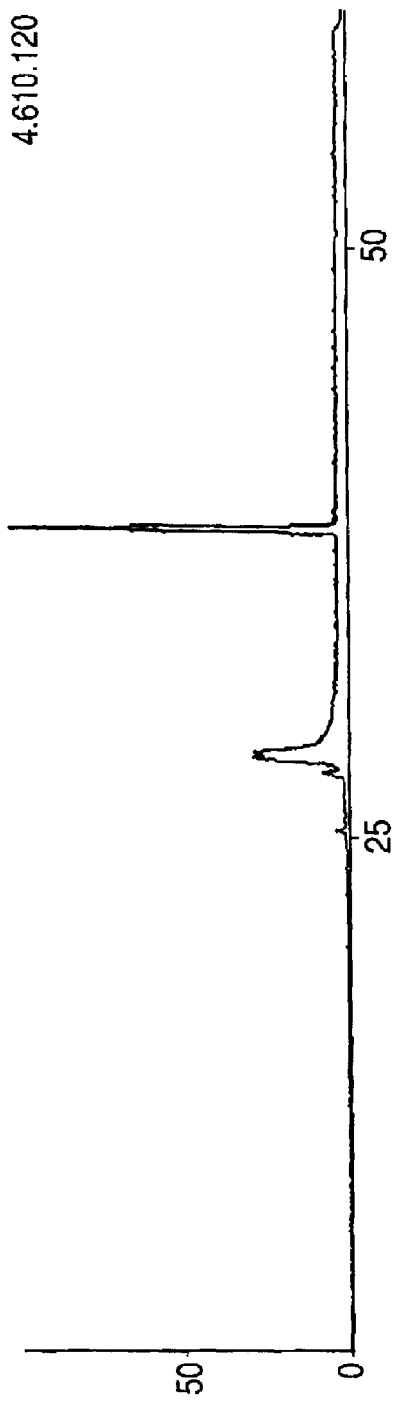
FIGS. 4A and 4B show results of GC-MS analysis of the outer shell of electrophoretic particles of Example 2.
Figure 4B:
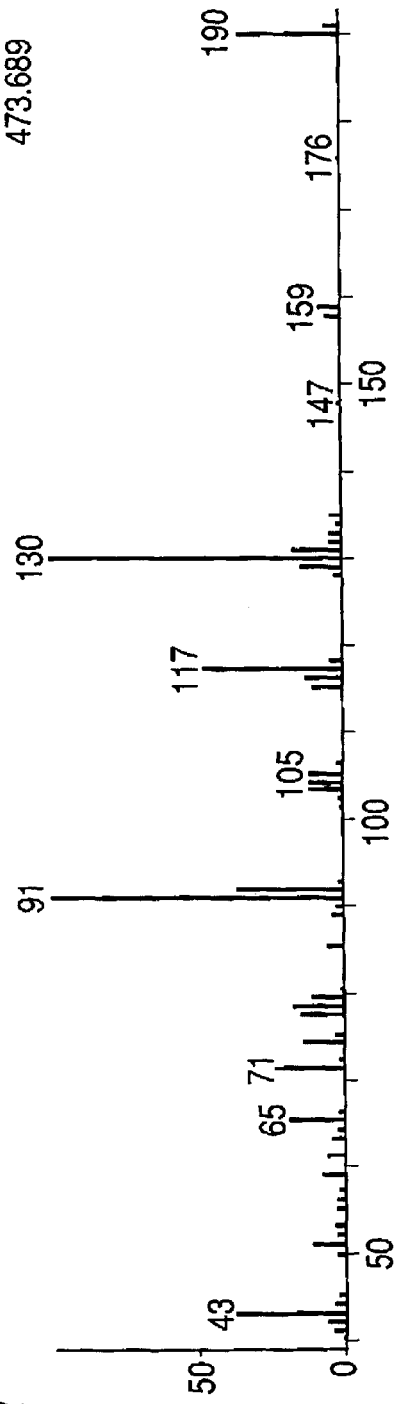

In addition, the electrophoretic particles were dried under reduced pressure, and were thereafter suspended in 20 ml of chloroform and stirred at 60° C. for 20 hours to extract PHA constituting shells. The extract was filtered through a membrane filter having a pore size of 0.45 μm, and was concentrated under reduced pressure by a rotary evaporator, followed by carrying out methanolysis in accordance with an ordinary method and conducting analyses by a gas chromatography-mass spectrometer (GC-MS, Shimadzu QP-5050, E1 method) to identify methyl-esterified PHA monomer units. As a result, the PHA was found to be PHA having 3-hydroxy-5-phenylvaleric acid as a monomer unit as shown in FIGS. 4A amd 4B. In addition, the molecular weight of the PHA was examined by gel permeation chromatography (GPC; Toso HLC-8020, column; Polymer laboratory PL gel MIXED-C (5 μm), solvent; chloroform, column temperature; 40° C., polystyrene equivalent) to obtain the result of Mn=16,000 and Mw=36,000.

According to the laser light scattering method, the electrophoretic particle was monodispersed with the average particle size of 1.6 μm.

EXAMPLE 3

Preparation of Electrophoretic Particles 3

As a pigment serving as a core, an azo based pigment, Pigment Yellow 12 and a condensation polycyclic pigment, Pigment Red 170 were suspended and dispersed in water in a same manner as Example 2. The PHA synthesizing enzyme derived from H45 and P161 strains prepared in Reference Example 2 was added to each pigment dispersion so that the concentration was 100 U/mL, and was left to stand at 20° C. for 30 minutes. Then, (R)-3-hydroxy-5-(4-fluorophenyl) valeryl CoA prepared in Reference 3 was added at a final concentration of 5 mM. A synthesis reaction was carried out by incubating the resulting solution at 37° C. for 30 minutes. Electrophoretic particles were collected, and were suspended with kerosene as a dispersion medium in the same manner as Example 2.

When the prepared electrophoretic particles were observed by a fluorescence microscope in a similar way to Example 2, fluorescence existed on the surfaces of the Pigment Yellow 12 particle and the Pigment Red particle 170, and therefore the electrophoretic particle was found to be a capsule structure with Pigment Yellow 12 and Pigment Red 170 as a core and PHA as a shell.

Figure 5A:
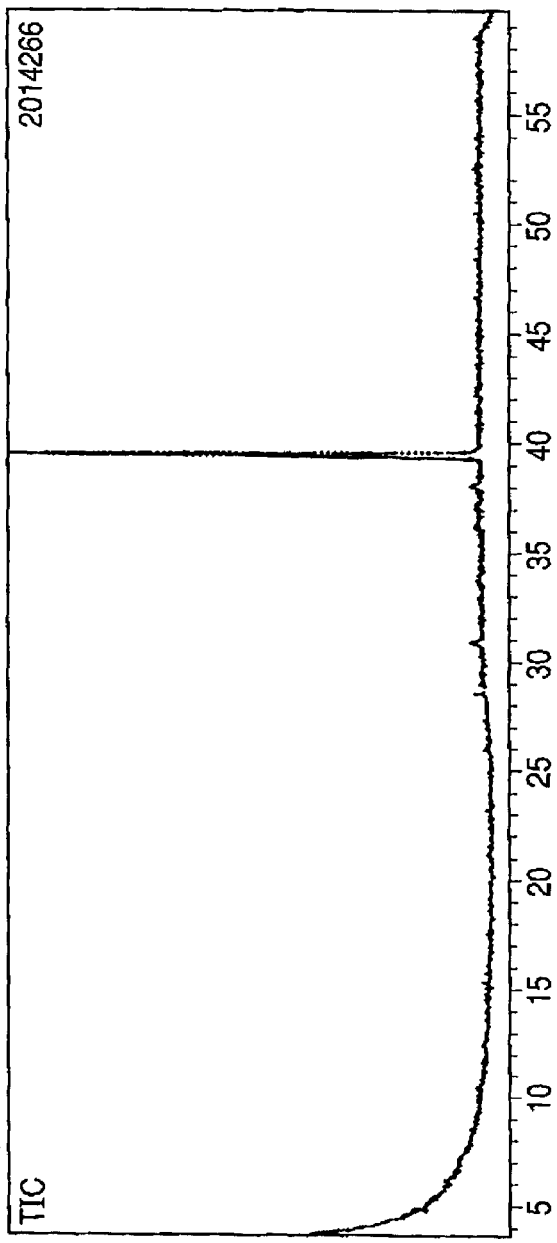
FIGS. 5A and 5B show results of GC-MS analysis of the outer shell of electrophoretic particles of Example 3.
Figure 5B:
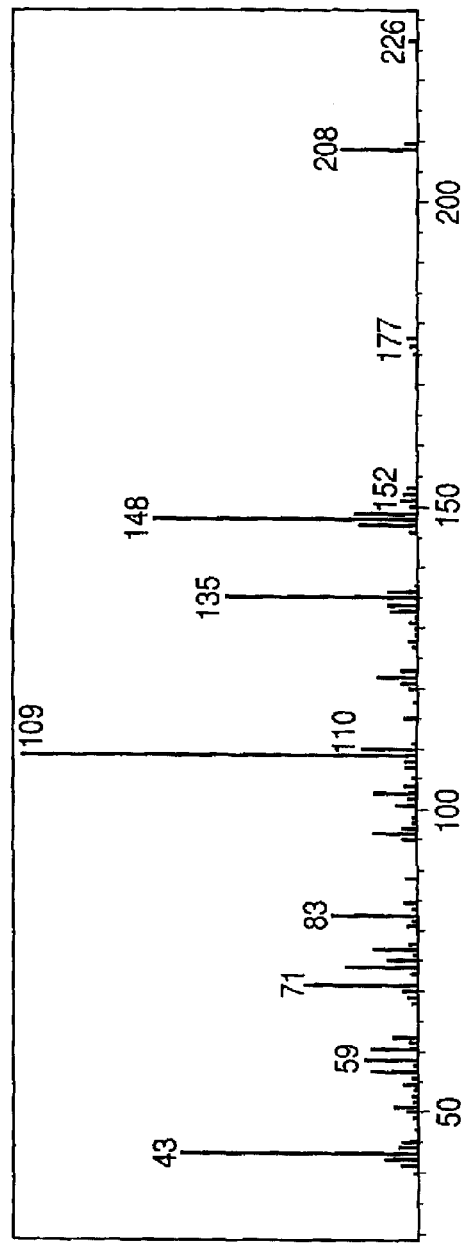

PHA constituting the shell of the electrophoretic particle was extracted to identify the methyl-esterified PHA monomer unit in a same manner as Example 2. As a result, the PHA was found to be PHA having (R)-3-hydroxy-5-(4-fluorophenyl) valeric acid as a monomer unit as shown in FIGS. 5A and 5B. In addition, the molecular weight of the PHA was examined by gel permeation chromatography (GPC; Toso HLC-8020, column; Polymer laboratory PL gel MIXED-C (5 μm), solvent; chloroform, column temperature; 40° C., polystyrene equivalent) to obtain the result of Mn=16,000, Mw=36,000 and Mn=17,000 and Mw=37,000.

According to the laser light scattering method, the electrophoretic particles were monodispersed with the average particle sizes of 1.6 μm and 1.7 μm, respectively.

EXAMPLE 4

Electrophoretic Display Device (Monochrome)

Figure 2B:
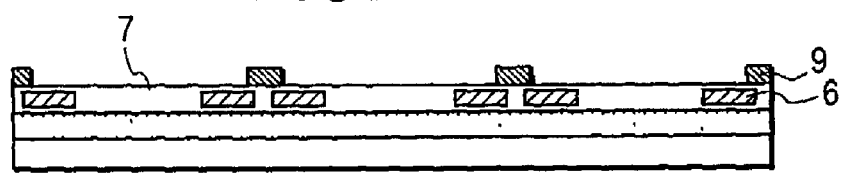

This example will be described using FIGS. 2A to 2D. An ITO electrode 5 was deposited on an optically transparent first substrate 1 composed of a PES film with thickness of 150 μm, and was patterned into a line by photolithography and wet etching (FIG. 2A). A resin layer containing titanium oxide fine particles irregularly reflecting light to exhibit white color was formed thereon as an insulating layer 7. Further, titanium carbide was deposited as a second electrode 6, and was shaped into a line by photolithography and dry etching, and only the first electrode 5 was etched in a circular form to bore a hole therein. Further a highly transparent polyimide layer was formed as an insulating layer 7 on the second electrode 6. Then, a heat sealable adhesive layer 9 was formed in a pattern on the joint with a second substrate 2 (FIG. 2B).

Figure 2C:
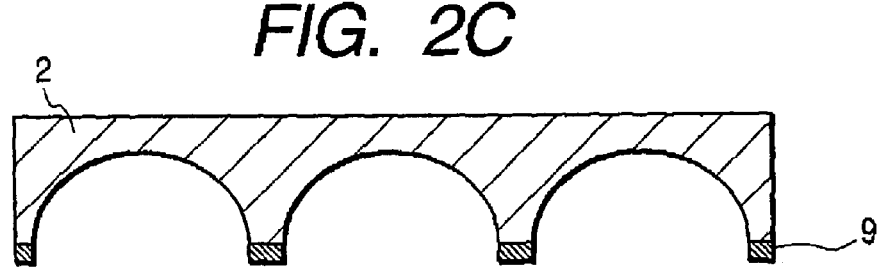
Figure 2D:
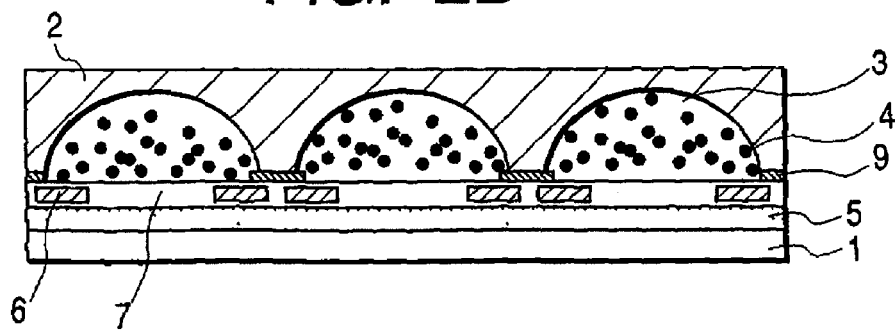

The optically transparent second substrate 2 composed of PES film was shaped into a concave by thermal press molding and the heat sealable adhesive layer 9 was formed on the joint with the first substrate 1 as in the case of the first substrate 1 (FIG. 2C). Then, a transparent insulating liquid 3 and electrophoretic particles 4 were loaded in the recess of the second substrate 2 was used. For the insulating liquid 3, diiodomethane having a greater refractivity than that of the PES film constituting the second substrate 2 was used. For the electrophoretic particles 4, the capsule structure with carbon black as a core and PHA as a shell having 3-hydroxyoctanoic acid as a monomer unit, and with the average particle size of 1.8 μm, prepared in Example 1, was used. After loading them, the adhesive layers 9 of the first substrate 1 and the second substrate 2 were aligned with each other, and were thermally bonded together. A voltage application circuit (not shown) was provided therein to form a display device (FIG. 2D).

Then, the prepared display device was used to provide display. The applied voltage was set to ±50V. When a voltage was applied so that the first electrode 5 was a positive electrode and the second electrode 6 was a negative electrode, positively charged electrophoretic particles 4 were moved onto the second electrode 6 located in the periphery of the bottom of the concave structure of the second substrate 2. When this was observed from the second substrate 2, the concave structure of the second substrate 2 acted as a lens, and therefore light was focused on the central part of the first substrate 1, and was let in the exposed white insulating layer 7, and the entire lens turned white.

On the other hand, when for reversing the polarity, a voltage was applied so that the first electrode 5 was a negative electrode and the second electrode 6 was a positive electrode, electrophoretic particles 4 were collected on the central part, and the entire lens turned black, the color of electrophoretic particles 4. The response speed at this time was 20 m/sec or lower, thus making it possible to prepare a display device capable of providing bicolor display.

EXAMPLE 5

Electrophoretic Display Device (Color)

An electrophoretic display device was prepared in the same manner as the step shown in Example 4. However, for electrophoretic particles 4, the capsule structure with carbon black as a core and PHA as a shell having 3-hydroxyoctanoic acid as a monomer unit, prepared in Example 1, the capsule structure with Pigment Blue 60 as a core and PHA as a shell having 3-hydroxy-5-phenyl valeric acid as a monomer unit, prepared in Example 2, and the capsule structure with Pigment yellow 12 or Pigment Red 170 as a core and PHA as a shell having 3-hydroxy-5-(4-fluorophenyl) valeric acid as a monomer unit, prepared in Example 3, were used.

The prepared display device was used to provide color display. The applied voltage was set to ±50V. When a voltage was applied so that the first electrode 5 was a positive electrode and the second electrode 6 was a negative electrode, positively charged electrophoretic particles 4 were moved onto the second electrode 6 located in the periphery of the bottom of the concave structure of the second substrate 2. When this was observed from the second substrate 2, the concave structure of the second substrate 2 acted as a lens, and therefore light was focused on the central part of the first substrate 1, and was let in the exposed white insulating layer 7, and the entire lens turned white.

On the other hand, when for reversing the polarity, a voltage was applied so that the first electrode 5 was a negative electrode and the second electrode 6 was a positive electrode, electrophoretic particles 4 were collected on the central part, and the entire lens turned black, blue, red or yellow, namely the color of electrophoretic particles 4. The response speed at this time was 20 m/sec or lower, thus making it possible to prepare a display device capable of providing color display.

EXAMPLE 6

Comparison of Dispersibility and Dispersion Stability with Time for Insulating Medium Dispersion stability was compared in the following manner between electrophoretic particles of the present invention and unprocessed electrophoretic particles. As a comparative example of electrophoretic particles not covered with polyhydroxyalkanoate, 25 g of carbon black was added to 75 g of thermally molten polyethylene resin, and was uniformly dispersed using a roll mill, followed by cold-curing to finely crush the same. A fraction with the average particle size of 1.5 μm remaining after sieving out the particles was dispersed in kerosene to provide a dispersion system for electrophoretic display. Three gram of electrophoretic particles as a test material, 50 ml of dispersion medium (kerosene), and 0.6 g of surfactant (polycarbonic acid derivative) if required were added in a test tube, and were stirred by a magnetic stirrer for 2 hours, followed by immediately weighing 1.0 ml of supernatant, and heating the same in an oven to measure the weight after complete removal of the dispersion medium. The weight at this time was Wo (g). Also, the above test tube was left to stand for a predetermined time period, followed by weighing 1.0 ml of supernatant, and heating the same in an oven to measure the weight after complete removal of the dispersion medium in a similar way. The weight at this time was Wi (g). Then, dispersion stability S was calculated in accordance with the following equation.

(Equation 1)

$$\text{Dispersion stability } S\ (\%) = Wi(g)/Wo(g) \times 100$$

The result of measuring dispersion stability S of electrophoretic particles of the present invention and unprocessed electrophoretic particles, determined in this way is shown in Table 3.

TABLE 3

|  | Dispersion Stability (after 20 minutes) |
|---|---|
| (Black) Electrophoretic Particles of the Invention Described in Example 1 | 99% |
| (Blue) Electrophoretic Particles of the Invention Described in Example 2 | 98% |
| (Yellow) Electrophoretic Particles of the Invention Described in Example 3 | 99% |
| (Red) Electrophoretic Particles of the Invention Described in Example 3 | 98% |
| Unprocessed Electrophoretic Particles | 2% |

As apparent from Table 3, the electrophoretic particles covered with PHA had significantly improved dispersion stability in the dispersion medium, compared to the unprocessed electrophoretic particles.

EXAMPLE 7

Preparation of Electrophoretic Particles

In the same manner as Example 3, as a pigment serving as a core, an azo based pigment, Pigment Yellow 12 and a condensation polycyclic pigment, Pigment Red 170 were used to prepare pigment dispersions and the PHA synthesizing enzyme derived from H45 strain and P161 strain was added to each of the pigment dispersions so that the concentration was 100 U/mL, and was left to stand at 20° C. for 30 minutes.

Then, (R)-3-hydroxy-5-(4-fluorophenyl) valeryl CoA prepared in Reference Example 3 was added at a final concentration of 5 mM, and was incubated at 37° C. for 25 minutes, followed by adding to this pigment dispersion (R)-3-hydroxy-5-phenoxyvaleryl CoA (prepared by the method described in Eur. J. Biochem., 250, 432–439 (1997) after obtaining 3-hydroxy-5-phenoxyvaleric acid by hydrolyzing 3-hydroxy-5-phenoxyvalerate obtained by Reformatsky reaction with zinc, using as raw materials 3-phenoxypropanal synthesized by the method described in J. Org. Chem., 55, 1490–1492 (1990) and ethyl bromoacetate) so that the final concentration was 1 mM, then incubating the same at 37° C. for 5 minutes. After the reaction, electrophoretic particles were collected and suspended with kerosene as a dispersion medium in a same manner as Example 2.

Then, the weight of the polymer formed on the surfaces of the obtained electrophoretic particles was measured by a time-of-flight secondary ion mass spectrometer (TOF-SIMS IV, manufactured by CAMECA Co., Ltd.). From the obtained mass spectrum, it was found that the surface of the electrophoretic particle was constituted by a copolymer of polyhydroxy-5-phenoxyvalerate and polyhydroxy-5-(4-fluorophenyl) valerate in the molar ratio of 1.4:1. In addition, after the surface of the electrophoretic particle was slightly cut out, the mass spectrum was measured by TOF-SIMS in a similar way, and it was found that the polymer constituting the electrophoretic particle changed to a homopolymer of polyhydroxy-5-(4-fluorophenyl) valerate. Thereby, the electrophoretic particle of the present invention was found to be an electrophoretic particle in which polyhydroxy-5-(4-fluorophenyl) valerate covering the pigment is covered with polyhydroxy-5-phenoxyvalerate.

In addition, the molecular weight of the PHA was examined by gel permeation chromatography (GPC; Toso HLC-8020, column; Polymer laboratory PL gel MIXED-C (5 μm), solvent; chloroform, column temperature; 40° C., polystyrene equivalent) to obtain the result of Mn=15,000 and Mw=32,000. In addition, according to the laser light scattering method, the electrophoretic particles were monodispersed with the average particle sizes of 1.7 μm and 1.6 μm, respectively.

For these electrophoretic particles, dispersion stability with time was evaluated in a same manner as Example 6, and it was found that these electrophoretic particles had dispersion stability of 96% and 95%, respectively, after 20 minutes, both exhibiting still high levels of dispersion stability, although slightly lower than that of the electrophoretic particle of Example 3.

Then, voltages of +50V and −50V were repeatedly applied for 5 seconds at intervals of one minute over one hour using the display device of Example 5, followed by observing electrophoretic particles being deposited onto the surface of the electrode.

As a result, the amount of electrophoretic particles deposited on the surface of the electrode in this Example was smaller, compared to the electrophoretic particles of Example 3. From this fact, it has been found that polyhydroxy-5-(4-fluorophenyl) valerate covering the pigment is covered with less adhesive polyhydroxy-5-phenoxyvalerate, whereby the antifouling property of electrophoretic particles can be improved.

EXAMPLE 8

Preparation of Electrophoretic Particles by hydrophilic PHA 1

In the same manner as Example 3, as a pigment serving as a core, an azo based pigment, Pigment Yellow 12 and a condensation polycyclic pigment, Pigment Red 170 were used to prepare pigment dispersions, the PHA synthesizing enzyme derived from H45 strain and P161 strain was added to each of the pigment dispersions so that the concentration was 100 U/mL, and was left to stand at 20° C. for 30 minutes.

Then, (R)-3-hydroxypimelyl CoA (prepared by the method described in J. Bacteriol., 182, 2753–2760 (2000)) was added at a final concentration of 5 mM, and was incubated at 37° C. for 30 minutes. After the reaction, electrophoretic particles were collected and suspended with kerosene as a dispersion medium in a same manner as Example 2.

Then, the weight of the polymer formed on the surfaces of the obtained electrophoretic particles was measured by a time-of-flight secondary ion mass spectrometer (TOF-SIMS IV, manufactured by CAMECA Co., Ltd.). From the obtained mass spectrum, it was found that the surface of this electrophoretic particle was constituted by a homopolymer of polyhydroxypimelate. In addition, the mass spectrum was measured by TOF-SIMS in a similar way while cutting gradually the surface of this electrophoretic particle by ion sputtering, and it was found that all the surface was constituted by a homopolymer of polyhydroxypimelate. Thereby it was found that the electrophoretic particle of this Comparative Example was an electrophoretic particle with a hydrophobic pigment directly covered with hydrophilic polyhydroxypimelate.

In addition, the molecular weight of the PHA was examined by gel permeation chromatography (GPC; Toso HLC-8020, column; Polymer laboratory PL gel MIXED-C (5 μm), solvent; chloroform, column temperature; 40° C., polystyrene equivalent) to obtain the result of Mn=17,000 and Mw=37,000. In addition, according to the laser light scattering method, the electrophoretic particles were monodispersed with the average particle sizes of 1.8 μm and 1.6 μm, respectively.

EXAMPLE 9

Preparation of Electrophoretic Particles by hydrophilic PHA 2

In the same manner as Example 3, as a pigment serving as a core, an azo based pigment, Pigment Yellow 12 and a condensation polycyclic pigment, Pigment Red 170 were used to prepare pigment dispersions, the PHA synthesizing enzyme derived from H45 strain and P161 strain was added to each of the pigment dispersions so that the concentration was 100 U/mL, and was left to stand at 20° C. for 30 minutes.

Then, (R)-3-hydroxyoctanoyl CoA (prepared by the method described in Eur. J. Biochem., 250, 432–439 (1997)) was added at a final concentration of 5 mM, and was incubated at 37° C. for 5 minutes, followed by adding (R)-3-hydroxypimelyl CoA (prepared by the method described in J. Bacteriol., 182, 2753–2760 (2000)) to this pigment dispersion at the rate of 1 mM a minute using a microtube pump (MP-3N manufactured by Tokyo Rikakikai Co., Ltd.), while conducting incubation at 37° C. After 25 minutes, electrophoretic particles were collected, and were suspended with kerosene as a dispersion medium in the same manner as Example 2.

Then, the weight of the polymer formed on the surfaces of the obtained electrophoretic particles was measured by a time-of-flight secondary ion mass spectrometer (TOF-SIMS IV, manufactured by CAMECA Co., Ltd.). From the obtained mass spectrum, it was found that the surface of the micro-capsulated pigment was constituted by a copolymer of polyhydroxypimelate and polyhydroxyoctanoate (molar ratio 18:1). In addition, the mass spectrum was measured by TOF-SIMS in a similar way while cutting out gradually the surface of the micro-capsulated pigment by ion sputtering, and it was found that the ratio of polyhydroxypimelate in the above described copolymer gradually decreased as the surface was cut out, and the polymer finally changed to a homopolymer of polyhydroxyoctanoate. Form this fact, it has been found that the micro-capsulated pigment of this Example is an electrophoretic particle in which the hydrophobic pigment is covered with hydrophobic polyhydrooctanoate, which is covered with a copolymer of polyhydroxyoctanoate and polyhydroxypimelate, with the ratio of hydrophilic polyhydroxypimelate being increased as the surface is approached.

In addition, the molecular weight of the PHA was examined by gel permeation chromatography (GPC; Toso HLC-8020, column; Polymer laboratory PL gel MIXED-C (5 μm), solvent; chloroform, column temperature; 40° C., polystyrene equivalent) to obtain the result of Mn=18,000 and Mw=38,000. In addition, according to the laser light scattering method, the electrophoretic particles were monodispersed with the average particle sizes of 1.9 μm and 1.7 μm, respectively.

EXAMPLE 10

Evaluation of Electrophoretic Particles of Examples 8 and 9

Dispersion stability with time was evaluated in the same manner as Example 6 for the case where electrophoretic particles of Examples 8 and 9 and unprocessed electrophoretic particles were directly used, and the case where the electrophoretic particles were vigorously stirred for 5 minutes by a vortex mixer. The result for the case where the electrophoretic particles were not stirred is shown in Table 4, and the result for the case where the electrophoretic particles were stirred is shown in Table 5.

TABLE 4

|  | Example 8 | Example 9 | Unprocessed |
|---|---|---|---|
| Pigment Yellow 12 | 98% | 97% | 82% |
| Pigment Red 170 | 98% | 98% | 78% |

TABLE 5

|  | Example 8 | Example 9 | Unprocessed |
|---|---|---|---|
| Pigment Yellow 12 | 91% | 97% | 83% |
| Pigment Red 170 | 93% | 97% | 77% |

As a result, in the case where the electrophoretic particles were not stirred, the electrophoretic particles of Examples 8 and 9 both showed high dispersion stability. On the other hand, the unprocessed electrophoretic particles showed low dispersion stability.

In the case where the electrophoretic particles were stirred, high dispersion stability was maintained for the electrophoretic particles of Example 9, while dispersion stability of the electrophoretic particles of Example 8 was lower compared to the case where the electrophoretic particles were not stirred. For the unprocessed electrophoretic particles, dispersion stability was, low as in the case where the electrophoretic particles were not stirred.

In addition, when the electrophoretic particles of Examples 8 and 9 subjected to stirring were observed by an optical microscope after they were stored, each electrophoretic particle was suitably dispersed for Example 9, while for Example 8, some electrophoretic particles were coagulated and there existed electrophoretic particles from which covering PHA was stripped.

From the above described fact, it has been found that an organic pigment is covered with PHA having a hydrophobic functional group with high affinity for the organic pigment, and the PHA is covered with a copolymer of hydrophobic PHA monomer unit and hydrophilic PHA monomer unit, with the ratio of the hydrophilic PHA monomer unit being increased as the surface is approached, whereby a hydrophilic PHA capsule capable of encapsulating the organic pigment more stably can be prepared.

EXAMPLE 11

Preparation of Electrophoretic Particles

Carbon black was suspended in the concentration of 25% by mass as a pigment in a 20 mM phosphate buffer solution (pH 7.0) with 1% by mass of Tween-20 added therein as a surfactant. They were mixed by a ball mill to prepare a dispersion of carbon black. According to the laser light scattering method, the carbon black was monodispersed with the average particle size of 1.2 μm.

The PHA synthesizing enzyme YN2-C1 derived from *Pseudomonas cichorii* YN2 prepared in Reference Example 1 was added to make a concentration was 100 U/mL, and was left to stand at 20° C. for 30 minutes to fix the enzyme to the carbon black. Then, (R,S)-3-hydroxy-5-phenoxyvaleryl CoA and (R,S)-3-hydroxy-7, 8-epoxyoctanoyl CoA prepared in Reference Example 3 were added so that the final concentrations were 4 mM and 1 mM, respectively. A synthesis reaction was carried out by incubating the resulting solution at 37° C. for 30 minutes.

When a very small amount of the above reaction solution was dyed with Nile blue A, a reagent having a property of binding specifically to PHA to emit fluorescence, and was then observed by a fluorescence microscope (330 to 380 nm excitation filter, 420 nm long path absorption filter, manufactured by Nikon Co., Ltd.), fluorescence existed on the surface of the carbon black particle, and therefore the electrophoretic particle was found to be a capsule structure with carbon black as a core and PHA as a shell.

In addition, a part of the above reaction solution was collected by centrifugation (10,000×g, 4° C., 10 minutes) and dried under reduced pressure, and thereafter was suspended in chloroform and stirred at 60° C. for 20 hours to extract PHA constituting the shell. For this extracted solution, $^1$H-NMR analysis was carried out (Apparatus: FT-NMR: Bruker DPX 400, Measured nuclear specie: $^1$H, Solvent: heavy chloroform (containing TMS)). For the unit content (%) of each side chain unit calculated from this measurement, the content of 3-hydroxy-5-phenoxyvaleric acid unit was 83%, and the content of 3-hydroxy-7,8-epoxyoctanoic acid unit was 17%.

Operation of subjecting the above reaction solution to centrifugation (10,000×g, 4° C., 10 minutes), and suspending the precipitate in purified water was conducted three times, followed by dissolving therein hexamethylene diamine as a crosslinking agent in a ratio of 0.5 part by mass of hexamethylene diamine to one part of carbon black in the suspension. After ensuring it was dissolved, water was removed by freeze-drying (referred to as Particle 1). Particle 1 was reacted at 70° C. for 12 hours (referred to as Particle 2).

The above Particles 1 and 2 were suspended in chloroform, and was stirred at 60° C. for 20 hours to extract PHA constituting the shell, and chloroform was removed by drying under reduced pressure, followed by carrying out measurements using a differential scanning calorimeter (DSC; Pyris 1 manufactured by PerkinElmer Co., Ltd., rate of temperature rise: 10° C./minute). As a result, for Particle 1, a clear exothermic peak was observed near 90° C., showing that reaction between an epoxy group in the polymer and hexamethylene diamine occurred and crosslinking between polymers progressed. For Particle 2, on the other hand, a clear heat flow was not found, showing that the crosslinking reaction was almost completed.

In addition, infrared absorption was measured for a similar sample (FT-IR; 1720X manufactured by PerkinElmer Co., Ltd.). As a result, the peaks of amine (near 3340 cm$^{-1}$) and epoxy (near 822 cm$^{-1}$) found for Particle 1 disappeared for Particle 2.

From the above results, it has been apparent that a crosslinked polymer can be obtained by reacting PHA having an epoxy unit on the side chain with hexamethylene diamine.

On the other hand, a sample was prepared and examined in a same manner as described above except that (R)-3-hydroxyoctanoyl CoA was used instead of (R,S)-3-hydroxy-7, 8-epoxyoctanoyl CoA, but a result clearly showing crosslinking between polymers as described above was not obtained.

The above Particle 2 was resuspended in ethanol, followed by collecting the micro-capsulated pigment of Particle 2 again by centrifugation operation. This operation was conducted three times to dehydrate the pigment to provide electrophoretic particles. Then the electrophoretic particles were suspended with kerosene, and was repeatedly subjected to centrifugation and washing to substitute the dispersion medium for kerosene.

The above described macro-capsulated pigment was suspended in hexane, methanol, propylene glycol monomethyletheracetate or ethylether, and was stored at a room temperature for 30 days, but no substantial change was found in any of these solvents, showing that the micro-capsulated pigment had satisfactory chemical resistance. Thus, it has been found that the micro-capsulated pigment is capable of being used in many types of dispersion media. Also, the above described electrophoretic particle had satisfactory mechanical strength and heat resistance.

EXAMPLE 12

Electrophoretic Display Device

An electrophoretic display device was prepared to provide display in a same manner as Example 4, except that the electrophoretic particles of Example 11 were used as electrophoretic particles. The applied voltage was set to ±50V.

When a voltage was applied so that the first electrode 5 was a positive electrode and the second electrode 6 was a negative electrode, positively charged electrophoretic particles 4 were moved onto the second electrode 6 located in the periphery of the bottom of the concave structure of the second substrate 2. When this was observed from the second substrate 2, the concave structure of the second substrate 2 acted as a lens, and therefore light was focused on the central part of the first substrate 1, and was let in the exposed white insulating layer 7, and the entire lens turned white.

On the other hand, when for reversing the polarity, a voltage was applied so that the first electrode 5 was a negative electrode and the second electrode 6 was a positive electrode, electrophoretic particles 4 were collected on the central part, and the entire lens turned black, the color of electrophoretic particles 4. The response speed at this time was 20 m/sec or lower, thus making it possible to prepare a display device capable of providing bicolor display.

EXAMPLE 13

Preparation of Electrophoretic Particles

The PHA synthesizing enzyme derived from the pYN2-C1 recombinant strain was fixed to the pigment in a same manner as Example 11 except that white pigment powders of titanium oxide (average particle size 0.5 μm) were used instead of carbon black. Then, (R,S)-3-hydroxy-5-phenoxyvaleryl CoA and (R,S)-3-hydroxy-7,8-epoxyoctanoyl CoA prepared in Reference Example 3 were added so that the final concentrations were 4 mM and 1 mM, respectively. A synthesis reaction was carried out by incubating the resulting solution at 37° C. for 30 minutes. The produced micro-capsulated pigment was filtered, washed and dried, and 10 parts by mass of amino terminal modified polysiloxane (modified silicone oil TSF 4700 manufactured by GE Toshiba Silicone Co., Ltd.) was added to one part by mass of the micro-capsulated pigment, and was reacted at 70° C. for 2 hours. Operation of suspending this in methanol and subjecting to centrifugation (10,000×g, 4° C., 20 minutes) was repeatedly conducted to carry out washing and drying, whereby a micro-capsulated pigment having a graft chain of polysiloxane was obtained.

The above micro-capsulated pigment was resuspended in methanol, followed by carrying out centrifugation again to collect the micro-capsulated pigment. This operation was conducted three times to dehydrate the pigment to provide electrophoretic particles. Then the electrophoretic particles were suspended with kerosene, and was repeatedly subjected to centrifugation and washing to substitute the dispersion medium for kerosene.

Furthermore, the above described electrophoretic particle has a graft chain of polysiloxane, and therefore its mechanical strength, weather resistance, light resistance, heat resistance and the like are excellent.

EXAMPLE 14

Electrophoretic Display Device

The electrophoretic particles of Example 13 were used to prepare an electrophoretic display device having the following structure.

An insulating medium composed of colored insulating liquid, and the electrophoretic particle dispersed in the insulating medium are held in a closed space surrounded by a display side transparent substrate and an opposite substrate and a partition wall. A transparent display electrode is placed on the display side transparent substrate of each closed space, and an opposite electrode is placed on the opposite substrate.

The process for production of the above described electrophoretic display device is as follows. For the display side transparent substrate and opposite substrate, glass substrates were used. For the transparent display electrode, indium tin oxide (ITO) was deposited by vacuum coating process in thickness of 200 nm, and for the opposite electrode, a Al coating was provided by vacuum coating process in thickness of 200 nm. Then, using a polymer resin as a partition wall material, the process of coating of a photosensitive polyimide varnish/exposure/wet development was repeated three times, thereby forming a partition wall with a height of 50 μm on the opposite substrate. Subsequently, the insulating medium and electrophoretic particles were loaded in the partition wall. Superfine particles of alumina and silica serving as polar ion absorbents were added in advance in the insulating medium by 0.5 wt %, respectively. For the insulating medium, silicone oil with anthraquinone based black dyes dispersed therein was used. Finally, the partition wall was bonded to the transparent display substrate with an adhesive to obtain a display device having the above described structure.

Then, the prepared display device was used to provide display. First, when a voltage of −50V was applied to the transparent display electrode and opposite electrode, electrophoretic particles dispersed in the insulating medium were migrated to and fixed on the display transparent electrode, and cells turned white, the color of the electrophoretic particles. Then, when a voltage of +50V was applied to the transparent display electrode and opposite electrode, electrophoretic particles dispersed in the insulating medium were migrated to and fixed on the opposite electrode, and cells turned black, the color of the insulating medium. The response speed at this time was 50 msec, thus making it possible to prepare a display device capable of providing bicolor display.

EXAMPLE 15

Evaluation of Electrophoretic Particles of Examples 8 and 9

Dispersion stability of the electrophoretic particles described in Examples 11 and 13 was evaluated in the same manner as Example 6 to obtain the result of S=99% for both cases, and the electrophoretic particles covered with grafted PHA showed significantly improved stability in the dispersion medium compared to unprocessed electrophoretic particles.

As described in detail above, according to the present invention, the electrophoretic particle is covered with polyhydroxyalkanoate with a pigment as a core, and is therefore prevented from being coagulated in a dispersion medium or being irreversibly deposited on an electrode irrespective of the type of pigment. The electrophoretic display device containing a dispersion system using such electrophoretic particles between electrode plates has an excellent display property and is highly reliable.

---

What is claimed is:

1. In an electrophoretic particle, the improvement wherein said electrophoretic particle comprises a pigment in which at least a part of the surface of the pigment is covered with polyhydroxyalkanoate.

2. The electrophoretic particle according to claim 1, wherein said polyhydroxyalkanoate is comprised of at least one selected from the group consisting of monomer units expressed by formulas [1] to [10]:

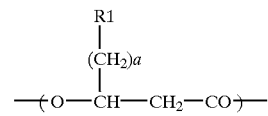 [1]

(wherein symbol "a" represents an integer, and the combination of R1 and "a" is selected from the group consisting of a combination of a hydrogen atom and any one integer selected from the group consisting of 0 to 10;

a combination of a halogen atom and any one integer selected from the group consisting of 1 to 10;

a combination of a chromophoric group and any one integer selected from the group consisting of 1 to 10;

a combination of a carboxyl group or a salt thereof and any one integer selected from the group consisting of 1 to 10; and a combination of

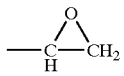

and any one integer selected from the group consisting of 1 to 7),

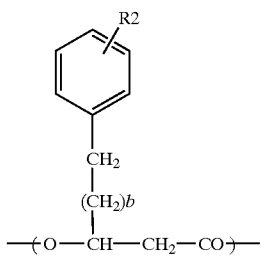

[2]

(wherein b represents any one integer selected from the group consisting of 0 to 7, and R2 is selected from the group consisting of a hydrogen atom (H), a halogen atom, —CN, —$NO_2$, —$CF_3$, —$C_2F_5$ and —$C_3F_7$),

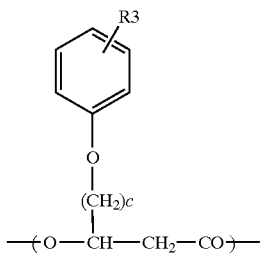

[3]

(wherein c represents any one integer selected from the group consisting of 1 to 8, and R3 is selected from the group consisting of a hydrogen atom (H), a halogen atom, —CN, —$NO_2$, —$CF_3$, —$C_2F_5$ and —$C_3F_7$),

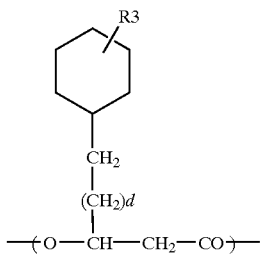

[4]

(wherein d represents any one integer selected from the group consisting of 0 to 7, and R4 is selected from the group consisting of a hydrogen atom (H), a halogen atom, —CN, —$NO_2$, —$CF_3$, —$C_2F_5$ and —$C_3F_7$),

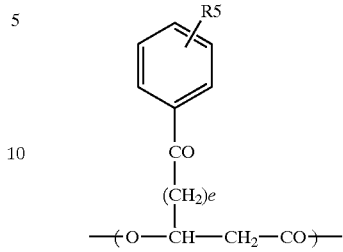

[5]

(wherein e represents any one integer selected from the group consisting of 1 to 8, and R5 is selected from the group consisting of a hydrogen atom (H), a halogen atom, —CN, —$NO_2$, —$CF_3$, —$C_2F_5$, $C_3F_7$, —$CH_3$, —$C_2H_5$ and —$C_3H_7$),

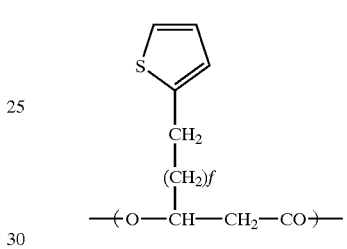

[6]

(wherein f represents any one integer selected from the group consisting of 0 to 7),

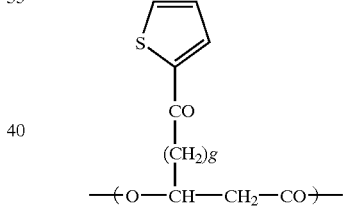

[7]

(wherein g represents any one integer selected from the group consisting of 1 to 8),

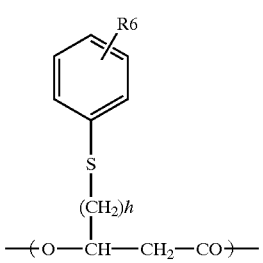

[8]

(wherein h represents any one integer selected from the group consisting of 1 to 7, and R6 is selected from the group consisting of a hydrogen atom (H), a halogen atom, —CN, —$NO_2$, —COOR', —$SO_2$R", —$CH_3$, —$C_2H_5$, —$C_3H_7$, —CH($CH_3$)$_2$ and —C($CH_3$)$_3$, wherein R' is selected from the group consisting of a hydrogen atom (H), Na, K, —$CH_3$ and —$C_2H_5$, and R" is selected from the group consisting of —OH, ONa, —OK, a halogen atom, —$OCH_3$ and —$OC_2H_5$),

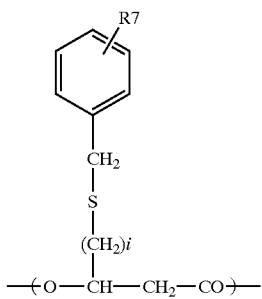

[9]

(wherein i represents any one integer selected from the group consisting of 1 to 7, and R7 is selected from the group consisting of a hydrogen atom (H), a halogen atom, —CN, —NO$_2$, —COOR' and —SO$_2$R", wherein R' is selected from the group consisting of a hydrogen atom (H), Na, K, —CH$_3$ and —C$_2$H$_5$, and R" is selected from the group consisting of —OH, —ONa, —OK, a halogen atom, —OCH$_3$ and —OC$_2$H$_5$), and

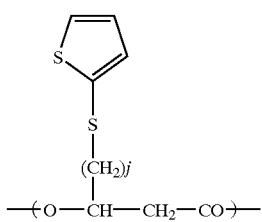

[10]

(wherein j represents any one integer selected from the group consisting of 1 to 9).

3. The electrophoretic particle according to claim 2, wherein a monomer unit composition of said polyhydroxyalkanoate is changed in the direction of from an inside of said electrophoretic particle to an outside thereof.

4. The electrophoretic particle according to claim 2, wherein at least a part of said polyhydroxyalkanoate is chemically modified.

5. The electrophoretic particle according to claim 4, wherein said chemically modified polyhydroxyalkanoate has at least a graft chain.

6. The electrophoretic particle according to claim 5, wherein said graft chain is formed by chemical modification of polyhydroxyalkanoate containing at least a monomer unit having an epoxy group.

7. The electrophoretic particle according to claim 6, wherein said graft chain is a graft chain of compounds each of which has an amino group.

8. The electrophoretic particle according to claim 7, wherein said compound having an amino group is an amino-terminal-modified compound.

9. The electrophoretic particle according to claim 8, wherein each of said amino-terminal-modified compounds is independently selected from the group consisting of polyvinyl amine, polyethylene imine and amino-terminal-modified polysiloxane.

10. The electrophoretic particle according to claim 4, wherein at least a part of said polyhydroxyalkanoate is crosslinked.

11. The electrophoretic particle according to claim 10, wherein said crosslinked polyhydroxyalkanoate is a polyhydroxyalkanoate in which a polyhydroxyalkanoate containing at least a monomer unit having an epoxy group is crosslinked.

12. The electrophoretic particle according to claim 11, wherein said crosslinked polyhydroxyalkanoate is a polyhydroxyalkanoate crosslinked with at least one selected from the group consisting of a diamine compound, succinic anhydride, 2-ethyl-4-methylimidazole and irradiation of electron ray.

13. The electrophoretic particle according to claim 12, wherein said diamine compound is hexamethylenediamine.

14. The electrophoretic particle according to claim 5, wherein said graft chain is a graft chain of compounds each of which has an amino group.

15. The electrophoretic particle according to claim 14, wherein said compound having an amino group is a amino-terminal-modified compound.

16. The electrophoretic particle according to claim 15, wherein each of said amino-terminal-modified compounds is independently selected from the group consisting of polyvinyl amine, polyethylene imine and amino-terminal-modified polysiloxane.

17. An electrophoretic display device having a structure in which a dispersion system of the electrophoretic particles according to any of claims 14 to 16 is enclosed in a space between a pair of electrode plates, and means for applying a voltage across said electrode plates to change the state of distribution of the electrophoretic particles in the dispersion system.

18. The electrophoretic particle according to any of claims 14 to 16, wherein the molecular weight of said polyhydroxyalkanoate is in the range of from 1000 to 10000000.

19. The electrophoretic particle according to claim 18, wherein the molecular weight of said polyhydroxyalkanoate is in the range of from 3000 to 1000000.

20. The electrophoretic particle according to claim 10, wherein said crosslinked polyhydroxyalkanoate is a polyhydroxyalkanoate crosslinked with at least one selected from the group consisting of a diamine compound, succinic anhydride, 2-ethyl-4-methylimidazole and irradiation of electron ray.

21. The electrophoretic particle according to claim 20, wherein said diamine compound is hexamethylenediamine.

22. An electrophoretic display device having a structure in which a dispersion system of the electrophoretic particles according to claim 20 or 21 is enclosed in a space between a pair of electrode plates, and means for applying a voltage across said electrode plates to change the state of distribution of the electrophoretic particles in the dispersion system.

23. The electrophoretic particle according to claim 20 or 21, wherein the molecular weight of said polyhydroxyalkanoate is in the range of from 1000 to 10000000.

24. The electrophoretic particle according to claim 23, wherein the molecular weight of said polyhydroxyalkanoate is in the range of from 3000 to 1000000.

25. An electrophoretic display device having a structure in which a dispersion system of the electrophoretic particles according to any of claims 1 to 13 is enclosed in a space between a pair of electrode plates, and means for applying a voltage across said electrode plates to change the state of distribution of the electrophoretic particles in the dispersion system.

26. The electrophoretic particle according to any of claims 1 to 13, wherein the molecular weight of said polyhydroxyalkanoate is in the range of from 1000 to 10000000.

27. The electrophoretic particle according to claim 26, wherein the molecular weight of said polyhydroxyalkanoate is in the range of from 3000 to 1000000.

28. A process for driving an electrophoretic display device comprising the steps of:

providing the electrophoretic display device having a structure in which a dispersion system of the electrophoretic particles according to any of claims 1 to 13 is enclosed in a space between a pair of electrode plates; and applying a voltage across said electrode plates to change the state of distribution of the electrophoretic particles in the dispersion system.

29. A process for preparing electrophoretic particles, comprising the step of:

carrying out a polyhydroxyalkanoate synthesis reaction with 3-hydroxyacyl CoA as a substrate in the presence of a polyhydroxyalkanoate synthesizing enzyme fixed on the surfaces of pigment particles dispersed in an aqueous medium, thereby at least part of the surface of the pigment particle is covered with polyhydroxyalkanoate to obtain electrophoretic particles.

30. The process according to claim 29, wherein the polyhydroxyalkanoate is comprised of at least one selected from the group consisting of monomer units expressed by formulas [1] to [10], and each corresponding 3-hydroxyacyl CoA is selected from the group consisting of 3-hydroxyacyl CoA expressed by formulas [11] to [20]:

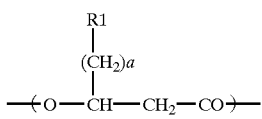
[1]

(wherein symbol "a" represents an integer, and the combination of R1 and "a" is selected from the group consisting of a combination of a hydrogen atom and any one integer selected from the group consisting of 0 to 10;

a combination of a halogen atom and any one integer selected from the group consisting of 1 to 10;

a combination of a chromophoric group and any one integer selected from the group consisting of 1 to 10;

a combination of a carboxyl group or a salt thereof and any one integer selected from the group consisting of 1 to 10; and a combination of

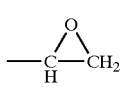

and any one integer selected from the group consisting of 1 to 7),

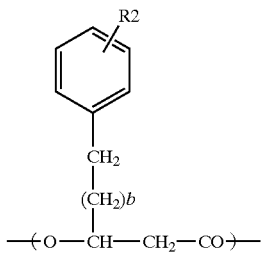
[2]

(wherein b represents any one integer selected from the group consisting of 0 to 7, and R2 is selected from the group consisting of a hydrogen atom (H), a halogen atom, —CN, —NO$_2$, —CF$_3$, —C$_2$F$_5$ and —C$_3$F$_7$),

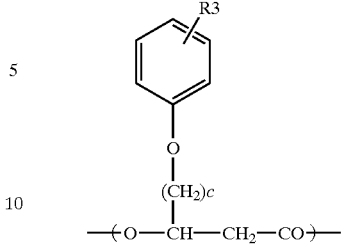
[3]

(wherein c represents any one integer selected from the group consisting of 1 to 8, and R3 is selected from the group consisting of a hydrogen atom (H), a halogen atom, —CN, —NO$_2$, —CF$_3$, —C$_2$F$_5$ and —C$_3$F$_7$),

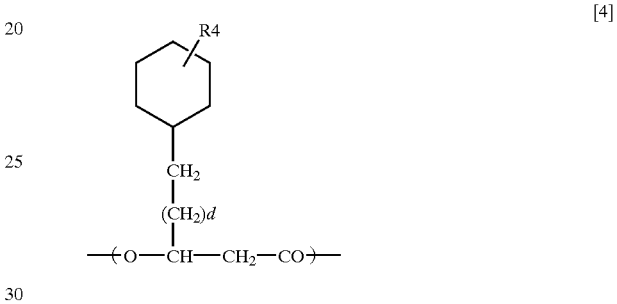
[4]

(wherein d represents any one integer selected from the group consisting of 0 to 7, and R4 is selected from the group consisting of a hydrogen atom (H), a halogen atom, —CN, —NO$_2$, —CF$_3$, —C$_2$F$_5$ and —C$_3$F$_7$),

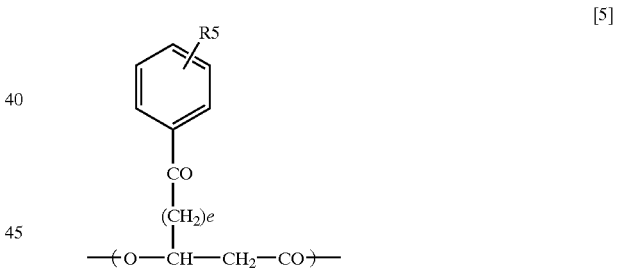
[5]

(wherein e represents any one integer selected from the group consisting of 1 to 8, and R5 is selected from the group consisting of a hydrogen atom (H), a halogen atom, —CN, —NO$_2$, —CF$_3$, —C$_2$F$_5$, C$_3$F$_7$, —CH$_3$, —C$_2$H$_5$ and —C$_3$H$_7$),

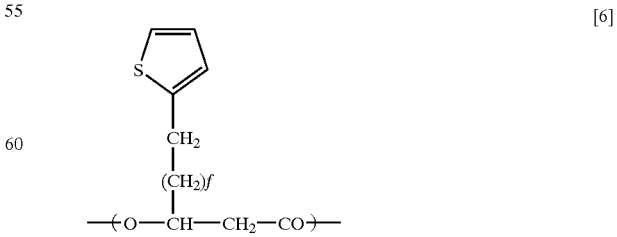
[6]

(wherein f represents any one integer selected from the group consisting of 0 to 7),

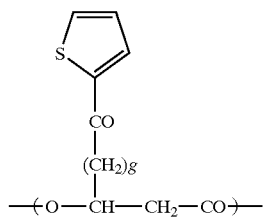

(wherein g represents any one integer selected from the group consisting of 1 to 8),

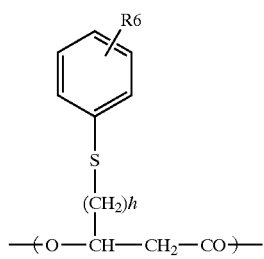

(wherein h represents any one integer selected from the group consisting of 1 to 7, and R6 is selected from the group consisting of a hydrogen atom (H), a halogen atom, —CN, —NO$_2$, —COOR', —SO$_2$R", —CH$_3$, —C$_2$H$_5$, —C$_3$H$_7$, —CH(CH$_3$)$_2$ and —C(CH$_3$)$_3$, wherein R' is selected from the group consisting of a hydrogen atom (H), Na, K, —CH$_3$ and —C$_2$H$_5$, and R" is selected from the group consisting of —OH, ONa, —OK, a halogen atom, —OCH$_3$ and —OC$_2$H$_5$),

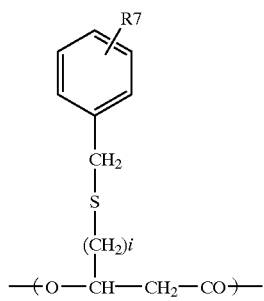

(wherein i represents any one integer selected from the group consisting of 1 to 7, and R7 is selected from the group consisting of a hydrogen atom (H), a halogen atom, —CN, —NO$_2$, —COOR' and —SO$_2$R", wherein R' is selected from the group consisting of a hydrogen atom (H), Na, K, —CH$_3$ and —C$_2$H$_5$, and R" is selected from the group consisting of —OH, —ONa, —OK, a halogen atom, —OCH$_3$ and —OC$_2$H$_5$), and

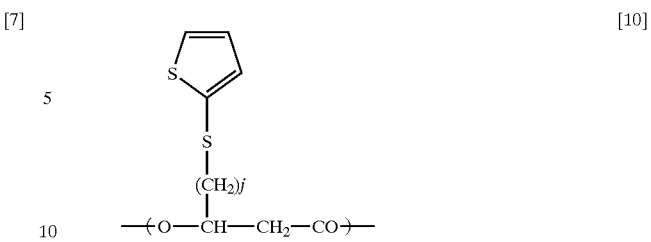

(wherein j represents any one integer selected from the group consisting of 1 to 9),

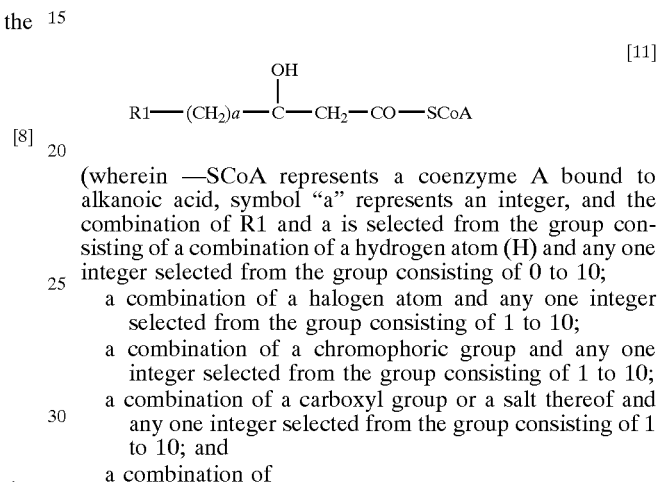

(wherein —SCoA represents a coenzyme A bound to alkanoic acid, symbol "a" represents an integer, and the combination of R1 and a is selected from the group consisting of a combination of a hydrogen atom (H) and any one integer selected from the group consisting of 0 to 10;
a combination of a halogen atom and any one integer selected from the group consisting of 1 to 10;
a combination of a chromophoric group and any one integer selected from the group consisting of 1 to 10;
a combination of a carboxyl group or a salt thereof and any one integer selected from the group consisting of 1 to 10; and
a combination of

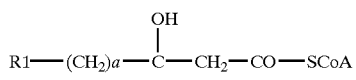

and any one integer selected from the group consisting of 1 to 7), and corresponds to R1 and a in the monomer unit expressed by said Formula [1],

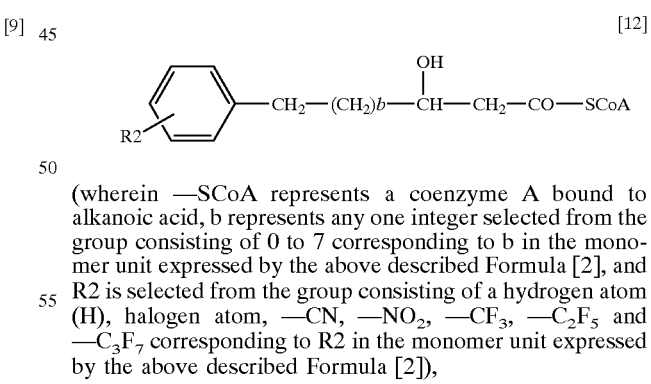

(wherein —SCoA represents a coenzyme A bound to alkanoic acid, b represents any one integer selected from the group consisting of 0 to 7 corresponding to b in the monomer unit expressed by the above described Formula [2], and R2 is selected from the group consisting of a hydrogen atom (H), halogen atom, —CN, —NO$_2$, —CF$_3$, —C$_2$F$_5$ and —C$_3$F$_7$ corresponding to R2 in the monomer unit expressed by the above described Formula [2]),

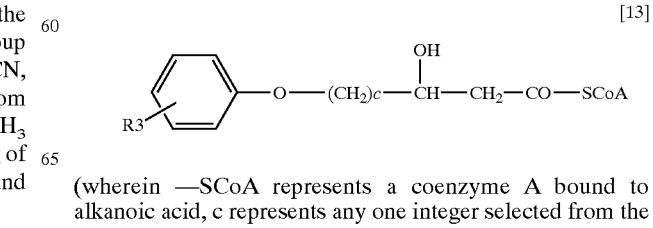

(wherein —SCoA represents a coenzyme A bound to alkanoic acid, c represents any one integer selected from the group consisting of 1 to 8 corresponding to c in the monomer unit expressed by the above described Formula [3], and R3 is selected from the group consisting of a hydrogen atom (H), halogen atom, —CN, —NO$_2$, —CF$_3$, —C$_2$F$_5$ and —C$_3$F$_7$ corresponding to R3 in the monomer unit expressed by the above described Formula [3]),

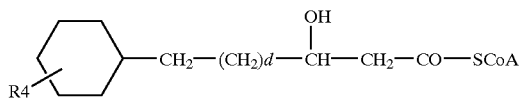

[14]

(wherein —SCoA represents a coenzyme A bound to alkanoic acid, d represents any one integer selected from the group consisting of 0 to 7 corresponding to d in the monomer unit expressed by the above described Formula [4], and R4 is selected from the group consisting of a hydrogen atom (H), halogen atom, —CN, —NO$_2$, —CF$_3$, —C$_2$F$_5$ and —C$_3$F$_7$ corresponding to R4 in the monomer unit expressed by the above described Formula [4]),

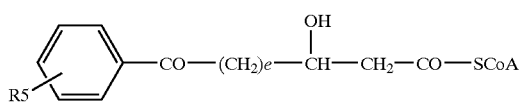

[15]

(wherein —SCoA represents a coenzyme A bound to alkanoic acid, e represents any one integer selected from the group consisting of 1 to 8 corresponding to e in the monomer unit expressed by the above described Formula [5], and R5 is selected from the group consisting of a hydrogen atom (H), halogen atom, —CN, —NO$_2$, —CF$_3$, —C$_2$F$_5$, —C$_3$F$_7$, —CH$_3$, —C$_2$H$_5$ and —C$_3$H$_7$ corresponding to R5 in the monomer unit expressed by the above described Formula [5]),

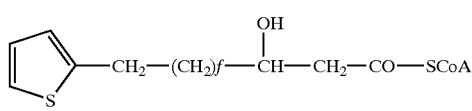

[16]

(wherein —SCoA represents a coenzyme A bound to alkanoic acid, and f represents any one integer selected from the group consisting of 0 to 7 corresponding to f in the monomer unit expressed by the above described Formula [6]),

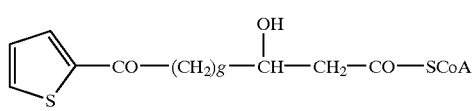

[17]

(wherein —SCoA represents a coenzyme A bound to alkanoic acid, and g represents any one integer selected from the group consisting of 1 to 8 corresponding to g in the monomer unit expressed by the above described Formula [7]),

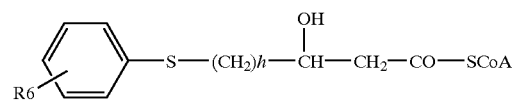

[18]

(wherein —SCoA represents a coenzyme A bound to alkanoic acid, h represents any one integer selected from the group consisting of 1 to 7 corresponding to h in the monomer unit expressed by the above described Formula [8], and R6 is selected from the group consisting of a hydrogen atom (H), halogen atom, —CN, —NO$_2$, —COOR', —SO$_2$R", —CH$_3$, —C$_2$H$_5$, —C$_3$H$_7$, —CH(CH$_3$)$_2$ and —C(CH$_3$)$_3$ corresponding to R6 in the monomer unit expressed by the above described Formula [8] wherein R' is selected from the group consisting of a hydrogen atom (H), Na, K, —CH$_3$ and —C$_2$H$_5$, and R" is selected from the group consisting of —OH, —ONa, —OK, a halogen atom, —OCH$_3$ and —OC$_2$H$_5$),

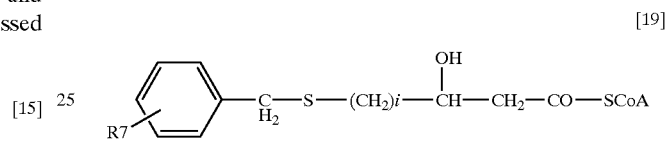

[19]

(wherein —SCoA represents a coenzyme A bound to alkanoic acid, i represents any one integer selected from the group consisting of 1 to 7 corresponding to i in the monomer unit expressed by the above described Formula [9], and R7 is selected from the group consisting of a hydrogen atom (H), halogen atom, —CN, —NO$_2$, —COOR' and —SO$_2$R" corresponding to R7 in the monomer unit expressed by the above described Formula [9] wherein R' is selected from the group consisting of a hydrogen atom (H), Na, K, —CH$_3$ and —C$_2$H$_5$, and R" represents any of —OH, —ONa, —OK, a halogen atom, —OCH$_3$ and —OC$_2$H$_5$), and

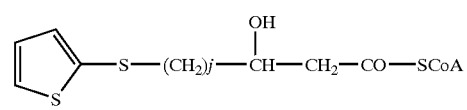

[20]

(wherein —SCoA represents a coenzyme A bound to alkanoic acid, and j represents any one integer selected from the group consisting of 1 to 9 corresponding to j in the monomer unit expressed by the above described Formula [10]).

31. The process according to claim 30, wherein the composition of said 3-hydroxyacyl coenzyme A is changed with time, whereby the composition of 3-hydroxyalkanoic acid unit of said polyhydroxyalkanoate is changed in the direction of from an inside of said electrophoretic particle to an outside thereof.

32. The process according to claim 30, which process further comprises a step of chemically modifying at least a part of polyhydroxyalkanoate with which said pigment particles are covered.

33. The process according to claim 32, wherein said chemically modifying step is a step of adding a graft chain to at least a part of polyhydroxyalkanoate.

34. The process according to claim 33, wherein said step of adding a graft chain is a step of reacting at least a part of polyhydroxyalkanoate with a compound having a reactive functional group at the terminal.

35. The process according to claim 34, wherein said polyhydroxyalkanoate contains at least a monomer unit having an epoxy group.

36. The process according to claim 34 or 35, wherein said compound having a reactive functional group at the terminal has an amino group.

37. The process according to claim 36, wherein said compound having an amino group is an amino-terminal-modified compound.

38. The process according to claim 37, wherein said amino-terminal-modified compound is selected from the group consisting of polyvinyl amine, polyethylene imine and amino-terminal-modified polysiloxane.

39. The process according to claim 32, wherein said chemically modifying step is a step of crosslinking at least a part of polyhydroxyalkanoate.

40. The process according to claim 39, wherein said crosslinking step is a step of reacting at least a part of polyhydroxyalkanoate with a crosslinking agent.

41. The process according to claim 40, wherein said polyhydroxyalkanoate contains at least a monomer unit having an epoxy group.

42. The process according to claim 40 or 41, wherein said crosslinking agent is at least one selected from the group consisting of a diamine compound, succinic anhydride and 2-methyl-4-methylimidazole.

43. The process according to claim 42, wherein said diamine compound is hexamethylene diamine.

44. The process according to claim 39, wherein said crosslinking step is a step of irradiating polyhydroxyalkanoate with electron rays.

45. The process according to claim 29 or 30, wherein the polyhydroxyalkanoate synthesizing enzyme is produced by a microorganism capable of producing the enzyme or a transformant having a gene associated with the production capability introduced in a host microorganism.

46. The process according to claim 45, wherein the microorganism capable of producing polyhydroxyalkanoate synthesizing enzyme is a microorganism belonging to *Pseudomonas* sp.

47. The process according to claim 46, wherein the microorganism capable of producing polyhydroxyalkanoate synthesizing enzyme is at least one microorganism selected from the group consisting of *Pseudomonas putida* P91 (FERM BP-7373), *Pseudomonas cichorii* H45 (FERM BP-7374), *Pseudomonas cichorii* YN2 (FERM BP-7375) and *Pseudomonas jessenii* P161 (FERM BP-7376).

48. The process according to claim 45, wherein the microorganism capable of producing polyhydroxyalkanoate synthesizing enzyme is a microorganism belonging to *Burkholderia* sp.

49. The process according to claim 48, wherein the microorganism capable of producing polyhydroxyalkanoate synthesizing enzyme is at least one microorganism selected from the group consisting of *Burkholderia cepacia* KK01 (FERM BP-4235), *Burkholderia* sp. OK3 (FERM P-17370) and *Burkholderia* sp. OK4 (FERM P-17371).

50. The process according to claim 45, wherein the microorganism capable of producing polyhydroxyalkanoate synthesizing enzyme is a microorganism belonging to *Alcaligenes* sp.

51. The process according to claim 50, wherein the microorganism capable of producing polyhydroxyalkanoate synthesizing enzyme is *Alcaligenes* sp. TL2 (FERM BP-6913).

52. The process according to claim 45, wherein the microorganism capable of producing polyhydroxyalkanoate synthesizing enzyme is a microorganism belonging to *Ralstonia* sp.

53. The process according to claim 52, wherein the microorganism capable of producing polyhydroxyalkanoate synthesizing enzyme is *Ralstonia eutropha* TB64 (FERM BP-6933).

54. The process according to claim 45, wherein said host microorganism is *Escherichia coli*.

* * * * *

UNITED STATES PATENT AND TRADEMARK OFFICE
CERTIFICATE OF CORRECTION

PATENT NO. : 6,853,477 B2
DATED : February 8, 2005
INVENTOR(S) : Tsuyoshi Nomoto et al.

It is certified that error appears in the above-identified patent and that said Letters Patent is hereby corrected as shown below:

<u>Title page,</u>
Item [56], References Cited, FOREIGN PATENT DOCUMENTS,
"JP 21889525 7/1990" should read -- JP 2-189525 7/1990 --; and "JP 2284128 11/1990" should read -- JP 2-284128 11/1990 --.

<u>Column 3,</u>
Line 29, "coverd" should read -- covered --.

<u>Column 7,</u>
Formula [6], should read:

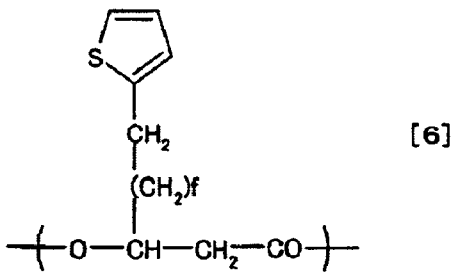

<u>Column 16,</u>
Line 15, "etc)" should read -- etc.) --.

<u>Column 23,</u>
Line 28, "describe" should read -- described --.

<u>Column 27,</u>
Line 8, "retains" should read -- retain --.

<u>Column 29,</u>
Line 20, ".Biotech)" should read -- .Biotech). --.

UNITED STATES PATENT AND TRADEMARK OFFICE
CERTIFICATE OF CORRECTION

PATENT NO.    : 6,853,477 B2
DATED         : February 8, 2005
INVENTOR(S)   : Tsuyoshi Nomoto et al.

It is certified that error appears in the above-identified patent and that said Letters Patent is hereby corrected as shown below:

<u>Column 57,</u>
Formula [4], that portion of the formula reading "R3" should read -- R4 --.

Signed and Sealed this

Thirty-first Day of January, 2006

JON W. DUDAS
*Director of the United States Patent and Trademark Office*